US011723617B2

(12) United States Patent
Fouras et al.

(10) Patent No.: US 11,723,617 B2
(45) Date of Patent: *Aug. 15, 2023

(54) METHOD AND SYSTEM FOR IMAGING

(71) Applicant: 4DMEDICAL LIMITED, Melbourne (AU)

(72) Inventors: Andreas Fouras, Woodland Hills, CA (US); Chaminda Rajeev Samarage, Melbourne (AU)

(73) Assignee: 4DMedical Limited, Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/683,064

(22) Filed: Feb. 28, 2022

(65) Prior Publication Data
US 2022/0183646 A1 Jun. 16, 2022

Related U.S. Application Data

(62) Division of application No. 16/081,854, filed as application No. PCT/AU2017/000054 on Feb. 24, 2017, now Pat. No. 11,278,256.

(30) Foreign Application Priority Data

Feb. 3, 2016 (AU) .................................. 2016900354
Mar. 4, 2016 (AU) .................................. 2016900817

(51) Int. Cl.
*A61B 6/00* (2006.01)
*G06T 7/143* (2017.01)
(Continued)

(52) U.S. Cl.
CPC ........ *A61B 6/5217* (2013.01); *A61B 5/02007* (2013.01); *A61B 5/08* (2013.01);
(Continued)

(58) Field of Classification Search
CPC ......... A61B 5/08; A61B 6/504; A61B 6/5217; G06T 7/11; G06T 7/187;
(Continued)

(56) References Cited

U.S. PATENT DOCUMENTS 5,491,642 A 2/1996 Wormell et al.
6,373,920 B1 4/2002 Hsieh
(Continued)

FOREIGN PATENT DOCUMENTS

DE 19948827 A1 4/2001
EP 2873371 A1 5/2015
(Continued)

OTHER PUBLICATIONS

Barker et al. "3-Component Phase-Contrast MRI WSS Vectors in the Carotid Bifurcation are Concurrent with Local Atherosclerotic Plaque Risk Hypotheses", Proc. Intl. Soc. Mag. Reson. Med. 18 (2010), p. 4384.
(Continued)

*Primary Examiner* — Jason M Ip
(74) *Attorney, Agent, or Firm* — Loza & Loza, LLP; David S. Sarisky

(57) ABSTRACT

The present invention relates to the field of medical imaging in the absence of contrast agents. In one form, the invention relates to the field of imaging vessels, particularly blood vessels such as the pulmonary vasculature and is suitable for use as a technique for detecting pulmonary embolism (PE), such as acute PE. Embodiments of the present invention provide improved image processing techniques having the capability to extract and use image data to overcome the need for contrast agents to distinguish between different types of tissue. Furthermore, it has also been realised that the image data accessed by the improved image processing can be used to identify irregularities in vessels.

14 Claims, 9 Drawing Sheets
(3 of 9 Drawing Sheet(s) Filed in Color)

(51) Int. Cl.

| | |
|---|---|
| *G06T 7/00* | (2017.01) |
| *G06T 7/187* | (2017.01) |
| *G06T 7/62* | (2017.01) |
| *A61B 5/08* | (2006.01) |
| *A61B 5/02* | (2006.01) |
| *G06T 7/35* | (2017.01) |
| *G06T 7/11* | (2017.01) |
| *A61B 6/03* | (2006.01) |
| *A61B 5/026* | (2006.01) |
| *A61B 5/00* | (2006.01) |
| *A61B 5/113* | (2006.01) |

(52) U.S. Cl.
CPC .............. *A61B 6/032* (2013.01); *A61B 6/481* (2013.01); *A61B 6/504* (2013.01); *A61B 6/507* (2013.01); *A61B 6/508* (2013.01); *A61B 6/541* (2013.01); *G06T 7/0012* (2013.01); *G06T 7/0016* (2013.01); *G06T 7/11* (2017.01); *G06T 7/143* (2017.01); *G06T 7/187* (2017.01); *G06T 7/35* (2017.01); *G06T 7/62* (2017.01); *A61B 5/026* (2013.01); *A61B 5/113* (2013.01); *A61B 5/7285* (2013.01); *A61B 2576/02* (2013.01); *G06T 2207/10076* (2013.01); *G06T 2207/10081* (2013.01); *G06T 2207/10088* (2013.01); *G06T 2207/10136* (2013.01); *G06T 2207/20016* (2013.01); *G06T 2207/20024* (2013.01); *G06T 2207/20076* (2013.01); *G06T 2207/30061* (2013.01); *G06T 2207/30101* (2013.01); *G06T 2207/30104* (2013.01); *G06T 2207/30172* (2013.01)

(58) Field of Classification Search
CPC . G06T 2207/10076; G06T 2207/20024; G06T 2207/20076; G06T 2207/10081; G06T 2207/30061; G06T 2207/30172
See application file for complete search history.

(56) References Cited

U.S. PATENT DOCUMENTS

| | | |
|---|---|---|
| 6,385,332 B1 | 5/2002 | Zahalka et al. |
| 6,549,646 B1 | 4/2003 | Yeh et al. |
| 6,631,716 B1 | 10/2003 | Robinson et al. |
| 6,650,928 B1 | 11/2003 | Gailly et al. |
| 6,816,607 B2 | 11/2004 | O'Donnell et al. |
| 7,333,643 B2 | 2/2008 | Murphy et al. |
| 7,376,253 B2 | 5/2008 | Spreeuwers et al. |
| 7,583,829 B2 | 9/2009 | Kiraly et al. |
| 7,668,357 B2 | 2/2010 | Keall et al. |
| 7,742,639 B2 | 6/2010 | Eck et al. |
| 7,876,936 B2 | 1/2011 | Raffy |
| 7,985,187 B2 | 7/2011 | Wibowo et al. |
| 8,090,176 B2 | 1/2012 | Kinnstaetter et al. |
| 8,175,358 B2 | 5/2012 | Weese et al. |
| 8,346,342 B2 | 1/2013 | Kalafut |
| 8,447,380 B2 | 5/2013 | Kuth et al. |
| 8,483,456 B2 | 7/2013 | Nagatsuka et al. |
| 8,538,111 B2 | 9/2013 | Zhang et al. |
| 8,553,832 B2 | 10/2013 | Camus et al. |
| 8,613,710 B2 | 12/2013 | Kolanko et al. |
| 8,666,139 B2 | 3/2014 | Zhang et al. |
| 8,668,652 B2 | 3/2014 | Wibowo et al. |
| 8,878,838 B2 | 11/2014 | Hautvast |
| 9,025,849 B2 | 5/2015 | Fouras et al. |
| 9,036,887 B2 | 5/2015 | Fouras |
| 9,044,194 B2 | 6/2015 | Noji et al. |
| 9,125,621 B2 | 9/2015 | Nagatsuka et al. |
| 9,198,628 B2 | 12/2015 | Shimada et al. |
| 9,254,112 B2 | 2/2016 | Tryggestad et al. |
| 9,289,140 B2 | 3/2016 | Ross et al. |
| 9,311,702 B2 | 4/2016 | Pautot |
| 9,760,989 B2 | 9/2017 | Yin et al. |
| 9,892,513 B2 | 2/2018 | Gurevich et al. |
| 9,962,086 B2 | 5/2018 | Dabbah et al. |
| 9,999,401 B2 | 6/2018 | Korporaal et al. |
| 2004/0092811 A1 | 5/2004 | Hill |
| 2005/0053267 A1 | 3/2005 | Mostafavi |
| 2005/0059876 A1 | 3/2005 | Krishnan et al. |
| 2005/0113672 A1 | 5/2005 | Salla |
| 2005/0187464 A1 | 8/2005 | Ho et al. |
| 2005/0240094 A1 | 10/2005 | Pinchon et al. |
| 2007/0092864 A1 | 4/2007 | Reinhardt et al. |
| 2008/0031404 A1 | 2/2008 | Khamene et al. |
| 2008/0077038 A1 | 3/2008 | Mcdonough |
| 2008/0181481 A1 | 7/2008 | Hong et al. |
| 2008/0193904 A1 | 8/2008 | Santhanam et al. |
| 2008/0269592 A1 | 10/2008 | Kuth et al. |
| 2009/0003511 A1 | 1/2009 | Roy et al. |
| 2009/0207968 A1 | 8/2009 | Grass |
| 2009/0208084 A1 | 8/2009 | Liu et al. |
| 2009/0252394 A1 | 10/2009 | Liang et al. |
| 2010/0041992 A1 | 2/2010 | Ohuchi et al. |
| 2010/0063410 A1 | 3/2010 | Avila |
| 2010/0191131 A1 | 7/2010 | Revishvili et al. |
| 2010/0228143 A1 | 9/2010 | Teschner |
| 2011/0051885 A1 | 3/2011 | Buelow et al. |
| 2012/0041318 A1 | 2/2012 | Taylor |
| 2013/0046176 A1 | 2/2013 | Mistretta et al. |
| 2013/0070062 A1 | 3/2013 | Fouras et al. |
| 2014/0192952 A1 | 7/2014 | Keall et al. |
| 2015/0320325 A1 | 11/2015 | Sheehan et al. |
| 2016/0095580 A1 | 4/2016 | Rubin |
| 2017/0309016 A1 | 10/2017 | Klaiman et al. |

FOREIGN PATENT DOCUMENTS

| | | |
|---|---|---|
| EP | 2299286 B1 | 9/2020 |
| JP | 2007089674 A | 4/2007 |
| JP | 2010046212 A | 3/2010 |
| KR | 1020040065846 A | 7/2004 |
| WO | 2006116178 A1 | 11/2006 |
| WO | 2008085048 A1 | 7/2008 |
| WO | 2011017739 A1 | 2/2011 |
| WO | 2011032210 A1 | 3/2011 |
| WO | 2012026145 A1 | 3/2012 |
| WO | 2013053000 A1 | 4/2013 |
| WO | 2013155556 A1 | 10/2013 |
| WO | 2014143974 A1 | 9/2014 |
| WO | 2015157799 A1 | 10/2015 |

OTHER PUBLICATIONS

Brahme et al. "4D laser camera for accurate patient positioning, collision avoidance, image fusion and adaptive approaches during diagnostic and therapeutic procedures", Int'l J. Physics Research & Practice. vol. 35:5 (May 2008) (2 pages).

Choi et al. "Numerical study of high-frequency oscillatory air flow and convective mixing in a CT-based human airway model", Annals Biomed. Engr. vol. 38:12, pp. 3550-3571 (Dec. 2010).

Christensen et al., "Tracking lung tissue motion and expansion/compression with inverse consistent image registration and spirometry", Int'l J. Med. Phys. Res.And Practice, vol. 34:6, Part 1 (first published May 21, 2007).

Cui et al. "Fluoroscopic gating without implanted fiducial markers for lung cancer radiotherapy based on support vector machines", Phys Med Biol, 53, (2008), pp. N315-27.

Docef et al. "Deformed CT reconstruction from limited projection data", Int'l Congress Series, vol. 1281 (May 2005), pp. 104-108.

Dubsky et al. "Three component, three dimensional X-ray particle image velocimetry using multiple projections", 14th Int Symp on Applications of Laser Techniques to Fluid Mechanics, Lisbon, Portugal (Jul. 7-10, 2008), 11 pages.

Dubsky et al. "Computed tomographic x-ray velocimetry for simultaneous 3D measurement of velocity and geometry in opaque vessels", Experiments In Fluids vol. 52:3, (Mar. 2012), pp. 104-108.

(56) References Cited

OTHER PUBLICATIONS

Dubsky et al. "Synchrotron-based dynamic computed tomography of tissue motion for regional lung function measurement", J. Royal Soc. Interface https://doi.org/10.1098/rsif.2012.0116 (Apr. 4, 2012), pp. 2213-2224.
Fouras et al. "Three-dimensional synchrotron x-ray particle image velocimetry", J. Applied Physics 102, (Sep. 28, 2007), pp. 064916-064916-6.
Fouras, et al. "The past, present, and future of x-ray technology for in vivo imaging of function and form", J. Applied Physics. 105, (2009), pp. 102009-102009-14.
Fouras et al. "In-vivo Synchrotron PIV for the measurement of airway motion", 8th Int'l Symposium on Particle Image Velocimetry-PIV09 Melbourne Victoria Australia (Aug. 25-28, 2009), (4 pages).
Fouras et al. "Engineering imaging: using particle image velocimetry to see physiology in a new light." Clinical & Experi. Pharmacology and Physiology 36, (2009), pp. 238-247.
Frangi et al. "Multiscale vessel enhancement filtering", Proc. 1998 MICCAI Int'l Conf. on Medical Image Computing and Computer-Assisted Intervention, Cambridge, Mass., (Oct. 11, 1998), (8 pages).
Guerrero et al. "Dynamic ventilation imaging from four-dimensional computed tomography", Physics in Medicine & Biology, vol. 51:4 (Jan. 25, 2006), pp. 777-791.
Irvine, et al. "Phase retrieval for improved three-dimensional velocimetry of dynamic x-ray blood speckle", Appl. Phys. Lett. 93, (Oct. 15, 2008), pp. 153901-15390-3.
Jimenez-Carretero et al. "3D frangi-based lung vessel enhancement filter penalizing airways", Proc. 2013 IEEE 10th International Symposium on Biomedical Imaging, San Francisco, CA, (Apr. 7, 2013), (4 pages).
Kim et al. "X-ray PIV measurements of blood flows without tracer particles", Experiments in Fluids, vol. 41:2, (Aug. 2006), pp. 195-200.
Liu et al. "Blood flow velocity and ultra-filtration velocity measured by CT imaging system inside a densely bundled hollow fiber dialyzer", Int'l J. of Heat and Mass Transfer. vol. 53:9-10, (Apr. 2010), pp. 1844-1850.
Orkisz et al. "Segmentation of the pulmonary vascular trees in 3D CT images using variational region-growing", iRBM, vol. 35:1, (Feb. 2014), pp. 11-19.
Qian et al. "A non-parametric vessel detection method for complex vascular structures", Medical Image Analysis, vol. 13, Issue 1, (Feb. 2009), pp. 49-61.
Rodriguez-Romero et al. "The influence of respiratory motion on CT image volume definition", Int. J. Med. Phys. Res. & Practice vol. 41:4 (Mar. 7, 2014), pp. 041701-041701-11.
Rudyanto et al. "Quantification of pulmonary vessel diameter in low-dose CT images", Proceedings vol. 414 Medical Imaging 2015, Computer-Aided Diagnosis Orlando, Florida, (Feb. 21, 2015), (6 pages).
Sato et al. "TEASAR: Tree-structure extraction algorithm for accurate and robust skeletons," Proc. 8th Pacific Conf. on Computer Graphics and Applications, Hong Kong, China, (2000), pp. 281-449.
Schindelin et al. "Fiji—an Open Source platform for biological image analysis", Nature Methods, vol. 9, No. 7, (Jun. 28, 2012), (15 pages).
Simon, "Regional ventilation and lung Mechanics Using X-Ray CT1", Academic Radiology vol. 12:11, X (Nov. 2005), pp. 281-449.
Soria et al. "Accuracy of out-of-plane vorticity component measurement using in-plane velocity vector field measurements", 12th Australasian Conference on Fluid Mechanics, Univ. Sydney, Australia (Dec. 10, 1995), pp. 387-390.
Soussen et al. "Polygonal and polyhedral contour reconstruction in computed tomography", IEEE Transactions on Image Processing, vol. 13:11 (Nov. 2004), pp. 1507-1523.
Staring et al. "Pulmonary vessel segmentation using vessel enhancement filters", Grand Challenge Website, available online at https://grand-challenge.org/site/VESSEL 12/Results/ insertresults/ public/20120328103241_163_LKEBChina_ VESSEL 12_StrainEnergy/algorithm_description.pdf, (Jan. 2012), (8 pages).
Sun et al. "Detection of central pulmonary embolism on non-contrast computed tomography: a case control study", Int'l J. Cardiovascular Imaging, vol. 30, No. 3, (Mar. 2014), (8 pages).
Thurgood et al. "Functional lung imaging during HFV in preterm rabbits", PLOS One; https://doi.org/10.1371/journal.pone.0048122 (Oct. 30, 2012), (9 pages).
Wiepütz et al. "Simultaneous Assessment of Airway Instability and Respiratory Dynamics with Low-Dose 4D-CT in Chronic Obstructive Pulmonary Disease: A Technical Note", Respiration 87:294-300 (2014), (7 pages).
Wittram et al. "CT Angiography of Pulmonary Embolism: Diagnostic Criteria and Causes of Misdiagnosis", RadioGraphics vol. 24, No. 5, 20 pp., (Sep. 1, 2004)., pp. 1219-1238.
Wong et al. "Cardiac flow component analysis", Medical Engr. & Physics vol. 32:2, (Mar. 2010), pp. 174-188.
Yin et al., "Simulation of pulmonary air flow with a subject-specific boundary condition", J. Biomechanics vol. 43:11, (Aug. 10, 2010), pp. 2159-2163.
Zhang et al. "Evaluation of segmentation algorithms for vessel wall detection in echo particle image velocimetry", IEEE Int'l Ultrasonics Symposium (DOI: 10.1109/ULTSYM.2009.5441630) (Sep. 20, 2009), pp. 2476-2479.
PCT/AU2012/001225, Int'l Prelim. Report on Patentability (dated Apr. 15, 2014), (10 pages).
PCT/AU2015/000219, Int'l Search Report (dated Jun. 4, 2015), (4 pages).
PCT/AU2013000390, Int'l Prelim. Report on Patentability (dated Oct. 21, 2014), (9 pages).
PCT/AU2018000028, Int'l Search Report & Written Opinion (dated Jun. 8, 2018), (17 pages).
PCT/AU2017/000054, Int'l Search Report (dated Jun. 22, 2017), (4 pages).

METHOD AND SYSTEM FOR IMAGING

CROSS-REFERENCE TO RELATED APPLICATION(S)

This application is a divisional application of U.S. patent application Ser. No. 16/081,854, filed Aug. 31, 2018, now U.S. Pat. No. 11,278,256, for "Method and System for Imaging," which is a U.S. National Phase of International Patent Application Serial No. PCT/AU2017/000054 entitled "Method and System for Imaging," filed on Feb. 24, 2017. International Patent Application Serial No. PCT/AU2017/000054 claims priority to Australian Patent Application No. 2016900354, filed on Feb. 3, 2016, and Australian Patent Application 2016900817, filed on Mar. 4, 2016. The entire contents of each of the above-cited applications are hereby incorporated by reference in their entirety for all purposes.

FIELD OF INVENTION

The present invention relates to the field of medical imaging in the absence of contrast agents.

In one form, the invention relates to the field of imaging vessels, particularly blood vessels such as the pulmonary vasculature.

In one particular aspect the present invention is suitable for use as a technique for detecting pulmonary embolism (PE), such as acute PE.

It will be convenient to hereinafter describe the invention in relation to detecting abnormalities in the pulmonary vasculature that correlate with PE, however it should be appreciated that the present invention is not so limited and can be used for the detection of other irregularities of pulmonary vasculature, or irregularities of other vasculature. Furthermore, although the invention is principally exemplified with reference to imaging of small animals for the purpose of investigative research, the invention is not so limited and is suitable for a wide range of human medical applications, as well as veterinary applications.

Furthermore, it will also be convenient to hereinafter describe the invention in relation to computed tomography (CT) however, it should be appreciated that the present invention is not limited to that imaging technique and could, for example, be used with other forms of imaging, including X-ray computed tomography (X-ray CT, often simply shortened to CT), particularly 4D-CT, MRI, ultrasound, or any other imaging method that acquires a three-dimensional (3D) image, or multiple 3D images over time. It will be understood that this includes techniques that acquire a series of two-dimensional (2D) images in order to create a 3D reconstruction.

BACKGROUND ART

It is to be appreciated that any discussion of documents, devices, acts or knowledge in this specification is included to explain the context of the present invention. Further, the discussion throughout this specification comes about due to the realisation of the inventor and/or the identification of certain related art problems by the inventor. Moreover, any discussion of material such as documents, devices, acts or knowledge in this specification is included to explain the context of the invention in terms of the inventor's knowledge and experience and, accordingly, any such discussion should not be taken as an admission that any of the material forms part of the prior art base or the common general knowledge in the relevant art in Australia, or elsewhere, on or before the priority date of the disclosure and claims herein.

In the past, X-ray CT has been extensively used in radiography to investigate the anatomy and function of internal organs such as the lungs. Digital geometry processing is routinely used to generate a three-dimensional (3D) image of the inside of the lung from a series of two-dimensional (2D) radiographic images taken around a single axis of rotation. CT uses computer processed X-rays to produce tomographic images (virtual 'slices') of specific areas of a lung.

In so-called 4D imaging, a time series of 3D images are collected. This can include acquiring a series of 2D images, and reconstructing a time series of 3D images from the 2D images. Specifically, in 4D X-ray CT, the X-ray slice data is generated using an X-ray source that rotates around a non-stationary object (e.g. a breathing human). X-ray detectors are positioned opposite to the X-ray source. It is possible to use a large range of X-ray CT devices to acquire 4D data. For example, standard, helical or spiral CT machines can be used to collect 4D data. Early versions of the imaging machines operated by rotating the X-ray source and detectors around a stationary patient. Following each complete rotation, the patient would be moved axially and the next rotation carried out. Newer machines have been designed to allow continuous rotation of the X-ray source and detectors while the patient is slowly and smoothly slid through the X-ray circular shroud. These are called helical or spiral CT machines.

A typical helical or spiral X-ray CT scan involves 10 to 50 rotations of the X-ray source around the patient, each coordinated with the table (on which the patient rests) moving through the circular shroud (which houses the X-ray source and X-ray detector). Fast scanning is carried out at a rate of about 4 rotations/sec, with the detector taking about 1000 'snapshots' per rotation. Each 'snapshot' is carried out at one position (angle, or projection angle) of the X-rays source. Typically between 40,000 to 200,000 images are collected in a 4D-CT.

CT can be used for imaging most body structures and is particularly useful for detecting both acute and chronic changes inside the lungs. However, the vasculature and changes to the vasculature (such as PE) are difficult to clearly visualise in and typically require the use of contrast agents such as iodine to enhance contrast and hence visibility.

PE is a blockage in the blood vessels of the lungs by a substance that has traveled from elsewhere in the body through the blood stream (embolism). Typically, PE is caused by the migration of a blood clot from a deep vein in an extremity (usually the legs) through the right side of the heart and into the pulmonary arteries. A small proportion of cases are caused by the embolisation of air, fat or amniotic fluid. PE is a common and sometimes fatal condition with mortality rates ranging from 14 to 28%.

To achieve the best outcomes for a patient with a PE, their PE requires rapid diagnosis and treatment. The obstruction of the blood flow through the lung vasculature, and the resultant pressure on the right ventricle of the heart, lead to the signs and symptoms of PE, such as difficulty in breathing, chest pain, heart palpitations, or possibly patient collapse. The clinical signs and symptoms provide some clues towards a diagnosis of PE, but ultimately a definitive diagnosis of PE requires imaging.

Contrast enhanced imaging, such as contrast enhanced computed tomography pulmonary angiography (CTPA) is rapidly replacing ventilation/perfusion scanning as the imaging modality of choice for diagnosing PE. A medical contrast agent is a substance that enhances the contrast of structure or fluids within the body in medical imaging, and thus enhances their visibility. However, adverse medical conditions can be caused by administration of contrast agents. Reactions can range from minor to severe. Risk factors for developing severe reactions include strong allergies, bronchial asthma, cardiac disease and use of certain drugs. Contrast medium induced nephropathy (CIN) is the third most common cause of in-hospital acute renal failure.

Many attempts have been made to improve the quality of pulmonary imaging. For example, U.S. Pat. No. 7,970,189 and US patent application 2011/0051885 (Buelow et al.) describe collecting pulmonary images, followed by segmentation of both the bronchus and arteries, including radii. The locations exhibiting visual anomalies are presented to a medical specialist, such as radiologist, for manual review and visual assessment to try and discern pulmonary problems, such as pulmonary embolism. Similarly U.S. Pat. No. 7,583,829 describes the use of segmentation of lung images and analysis of pulmonary sub-trees that may be affected by PE. However, these types of prior art imaging rely on the use of contrast agents to aid visualization (i.e. aid visualisation of the blood in the vasculature).

US patent application 2005/0240094 (Pichon et al) relates to visualization of a vascular tree structure from high-resolution contrast-enhanced computed tomography (CT) by segmenting the tree structure, then colouring the surface of the tree structure according to data associated with the internal tree structure, for example size data. The visualisation can then be manually reviewed.

US patent application 2009/0252394 (Liang et al.) teaches a method for detection of pulmonary emboli in CTPA. The method includes identifying a pulmonary emboli 'candidate' comprising a cluster of voxels, then determining if the 'candidate' is a true or a false positive, based on a spatial distribution of intensity values of the voxels in the cluster.

U.S. Pat. No. 7,876,936 (Raffy) teaches a method for processing a series of contrast enhanced CT sections of a pulmonary region to separate arteries from veins. The method includes interaction between a radiologist and a computer to separately identify pulmonary arteries and veins, computerised scanning of the vessels for characteristics of embolism, and comparison of the radiologist and computer data to produce a diagnosis. For example, this may include presenting pulmonary vasculature to the radiologist, who then traces the artery tree of interest. Automatic abnormality detection, based on the change in image intensity of the blood in the blood vessels, is then performed on the vessels of the traced tree to eliminate false positives associated with pulmonary veins.

Wittram et al. (Wittram et al. (2004) *CT Angiography of Pulmonary Embolism: Diagnostic Criteria and Causes of Misdiagnosis RadioGraphics*) teaches the typical procedure of using image intensity values for the computer aided detection of pulmonary emboli in CT angiography images with contrast. The existence of an embolus results in the following defects in CT angiography images:

a. Complete filling defects where contrast does not fill the vessel due to the existence of a large embolus. Image intensities downstream of the embolus are darker as there is no contrast in this part of the vessel, b. Partial filling defects where little contrast passes through and there are annular regions of high image intensity around the embolus, c. And other defects such as: wedge-shaped areas of hyperattenuation represent regions of lung infarction that are associated with loss of blood supply to that region of the lung; and contrast material flowing through thickened but smaller arteries that have re-opened (recanalization).

A publication by Staring et al. (Staring M et al. (2012) *Pulmonary vessel segmentation using vessel enhancement filters*, ISBI 2012 http://www.vessel12.grand-challenge.org) describes pulmonary vessel segmentation using Hessian-based multi-scale shape (vesselness) filters on imaging data, allowing manual inspection of the pulmonary vessels.

Rudyanto et al. (Rudyanto, R D et al. (2015) *Quantification of pulmonary vessel diameter in low-dose CT images* SPIE Medical Imaging 2015) describes a method for quantification of the diameter of plastic, rubber and silicone tubes using the scale of a multi-scale shape (vesselness) filter.

Jimenez Carretero et al. (Jimenez-Carretero et al. (2013) 3D *Frangi-based lung vessel enhancement filter penalizing airways* IEEE 10th International Symposium on Biomedical Imaging USA 2013) describe a method for segmenting vasculature utilizing the Frangi filter. The method involves identifying airway walls to allow removal of the airway wall before lung vessel segmentation. The method uses a single filtering framework to identify airway walls and lung vasculature.

Sun et al. (Sun et al. (2014) *Detection of central pulmonary embolism on non-contrast computed tomography: a case control study* International Journal of Cardiovascular Imaging) investigated the practicality of manual detection of embolism in the large central pulmonary arteries from contrast-free CT scans. The technique investigated requires a radiologist to assess the standard CT scans. The investigation found that non-contrast CT is not suitable for detecting central pulmonary embolism.

Therefore, there is a need for an improved method of using imaging as a diagnostic, particularly for irregularities in vasculature that are indicative of disease or other disorders.

SUMMARY OF INVENTION

It is an object of the embodiments described herein to overcome, or alleviate, at least one of the above noted drawbacks of related art systems, or to at least provide a useful alternative to related art systems.

In a first aspect of embodiments described herein there is provided a method of detecting an irregularity in lung vasculature, the method comprising the steps of:

(1) providing at least one image of a lung vasculature comprising one or more vessels, the at least one image having been captured in vivo in the absence of contrast agent, (2) applying a filter to the at least one image to create an output including a probability and scale field for the lung vasculature, and using one or two forms of the output to segment and quantify the geometry of the lung vasculature, (3) analysing the output in conjunction with geometric analysis to detect irregularities in the one or more vessels of the lung vasculature.

One embodiment of a typical method of the prior art is depicted in FIG. 1. While attempts have been made in the past to analyse images captured in the absence of contrast agent, none of the prior art studies have hitherto been successfully used for PE detection.

Preferably, in the method of the present invention, step (2) comprises the following sub-steps:

(2)(a) performing a Hessian-based multi-scale shape filter (as per Frangi 1998) on the image from step (1) to provide a probability field for the lung vasculature, (2)(b) carrying out flood-fill selection of the probability field for the lung vasculature to yield a binary image, (2)(c) carrying out binary segmentations of the binary image, and (2)(d) performing vessel centreline extraction from the binary segmentation, (2)(e) associating the scale from the shape filter (filter size which yields greatest probability that any given point on the image belongs to a tubular structure) to each point along the centreline of the vasculature tree to obtain local geometry data.

The at least one image may be any one or any combination of multiple 2D images and/or at least one 3D image.

It is envisaged that one or more of the above sub-steps may be included in the method, and that the method need not incorporate all of the above sub-steps.

In a preferred embodiment the irregularity detected is indicative of the presence of PE. Typically an embolism comprises a blood clot or air bubble, but may also comprise other foreign matter such as certain types of proteins or fats, or clumps of platelets, fibrin or other blood components as in a thrombotic embolism.

Vessel irregularity can be detected based on the diameter of one, or multiple, successive vessels in the vasculature. The filter used in the method, such as a Hessian-based multi-scale shape filter, provides a measure of the probability that a vessel of a given size exists at each image voxel. When measured at the centre of a vessel, the scale that gives the maximum probability of the vessel belonging to a tubular structure (i.e. the vessel's 'vesselness') represents the size, or calibre (diameter), of that vessel. Accordingly, the method of the present invention may include utilising the vessel centerlines and extracting the scale at which the greatest vesselness probability value exists at each centerline point. The term 'voxel' is well known in computer-based modelling or graphic simulation to refer to each of an array of elements of volume that constitute a notional three-dimensional space, especially each of an array of discrete elements into which a representation of a three-dimensional object is divided.

The irregularities detected by the method of the present invention could be used, for example, to classify segments (or portions) of the vasculature as (i) normal, (ii) PE present, and (iii) otherwise not normal, which may be indicative of other forms of lung or vascular disease. The irregularity detected will typically correspond to changes in vessel diameter. It is characteristic of PE that the vessel exhibits a distorted shape immediately adjacent to the embolism. For example, in the case of partial occlusion of the vessel, it is often characteristic of PE that the vessel bulges and has increased diameter 'upstream' of the embolism where blood pressure is increased, while 'downstream' from the embolism the vessel diameter is less than usual due to reduced blood pressure. And in the case of a complete occlusion of the vessel, the vessel may bulge outwards resulting in an increased vessel diameter following by a complete cut-off of vessel signal or discontinuity in the probability field. This type of irregularity may potentially act as a 'signature' to identify the nature of the PE.

The method of the present invention is particularly well adapted to the detection of irregularities in the pulmonary vasculature. This is due to the strong signal as detected by the Hessian filter, which is in turn due to the large differential between the low density of lung tissue, and the air therein, and the comparatively high density of pulmonary blood vessels.

The method of the present invention does not require the use of contrast agents that can cause adverse reactions in patients. Furthermore, because the method does not require a specific or unique imaging protocol, the method can be used to analyse previously acquired (contrast-free) imaging data, such as CT data in existing collections.

In a preferred embodiment, the method of the present invention additionally includes the step of segmenting the probability field for the lung vasculature from step (2).

Where used herein the term 'vascular segmentation' refers to the separation, or extraction, of the vasculature data from the 3D image. In particular, vessel segmentation may involve extracting the vasculature tree from the probability field. Segmentation can be performed on an anatomical or geometric basis. In some applications of the present invention geometric division will be adequate. Geometric division does not require additional anatomical information, and can be obtained at far less computer and labour cost (e.g. performing an image intensity threshold process). Alternatively, the segmentation may be associated with a particular region of the anatomy or anatomical feature (e.g. a region growing process in which a region of clearly identifiable vasculature is selected as the seed point). Segmentation on an anatomical basis is particularly preferred because, in comparison to imaging methods of the prior art, it is more physiologically and medically relevant, less arbitrary, and easier to use.

In another aspect of embodiments described herein there is provided an application stored on non-transitory medium adapted to enable detection of an irregularity in vasculature, said application comprising a predetermined instruction set adapted to enable the method steps of the present invention.

In yet a further aspect of embodiments described herein there is provided a computer readable storage medium for storing in non-transient form an application to enable segmentation of images of vasculature to provide segmented images and analysis of the segmented images to detect irregularities according to the method of the present invention.

In yet a further aspect of embodiments described herein there is provided an apparatus when used for the method of the invention, the apparatus comprising:

(i) one or more energy source;

(ii) one or more detectors for recording images of vasculature, the images being created by energy from the one or more energy sources passing through a sample comprising vasculature; and (iii) a sample retainer for locating the sample intermediate the one or more energy sources and the one or more detectors; wherein in use, the sample retainer rotates the sample through multiple energy projection angles and at least one image of vasculature is recorded at each of the projection angles to provide multiple images of the vasculature in the absence of a contrast agent.

Preferably the apparatus includes a processing means for carrying out steps 1 to 3 of the method described above. In a preferred embodiment the processing means is used for segmenting the images of vasculature to provide segmented images, and analysing the segmented images to detect irregularities in the vasculature.

In yet a further aspect of embodiments described herein there is provided an apparatus for use with the method described above, the apparatus comprising: (i) a rotatably mounted energy source; and (ii) a rotatably mounted detector positioned opposite the energy source for recording images of vasculature, the images being created by energy from the energy source passing through a sample having vasculature, wherein in use the detector and energy source rotate together about the sample, and the detector acquires an image of the vasculature at multiple projection angles to provide multiple images of the vasculature in the absence of a contrast agent. The apparatus may include a processing means for applying the filter and performing the geometric analysis.

In yet a further aspect of embodiments described herein there is provided a method of scanning for vascular irregularities in a three-dimensional in vivo image in the absence of contrast agent, the method including: applying a filter to the three-dimensional in vivo image to provide probability data and scale data; and performing an automated analysis on the probability data and/or the scale data to detect irregularities in the vasculature. When used herein the term "scanning for vascular irregularities" is intended to include searching, probing, examining, investigating, detecting, identifying etc. vascular irregularities, and is intended, in a preferred embodiment, to assist a user, such as a doctor, in quickly and accurately assessing whether a patient has vascular irregularities.

The method may include applying a shape filter to the three-dimensional in vivo image, preferably applying the shape filter at multiple scales, more preferably applying a Hessian based multi-scale shape filter, and more preferably where the Hessian multi-scale shape filter is applied as per Frangi 1998.

The step of performing automated analysis may include masking the scale field from data obtained from the probability field. The step of performing the automated geometric analysis may include comparing the scale at a first position to the scale at a second position, preferably where the first position and the second position are located in the same vessel branch, or in the same vessel generation. The automated geometric analysis may include comparing the scale at three positions, four positions, five positions, or six or more positions. The automated analysis may include fitting a function (or spline or similar), such as a polynomial, to scale values (or vessel diameters) from multiple points in a vessel branch. The coefficients of the fitted function, or other aspects of the fitted function, could then be inspected in order to detect vasculature irregularities, such as PE. A benefit of fitting a function to multiple scale values is that it may reduce "noise" in the scale data. Another benefit of fitting a function to multiple scale values is that it may provide an easier approach to determining and detecting a "signature" for vasculature irregularities, such as PE.

The method may include performing vessel segmentation on the probably field to extract a vasculature tree from the three-dimensional in vivo image, preferably mapping the scale field to the segmented vasculature tree to quantify the geometry of the vasculature tree.

The method may include acquiring a three-dimensional in vivo image in the absence of contrast agent.

In yet a further aspect of embodiments described herein there is provided a method of scanning for vascular irregularities in a three-dimensional in vivo image in the absence of contrast agent, the method including: applying a filter to the three-dimensional in vivo image to provide a probability field and a scale field; performing vessel segmentation on the probably field to extract a vasculature tree from the probability field; mapping the scale field to the segmented vasculature tree to quantify the geometry of the vasculature tree; and performing an automated geometric analysis on the calculated geometry to detect irregularities in the vasculature.

The step of segmenting the vasculature may include performing a region growing operation on the probability field, preferably the region growing operation is a flood filling operation, preferably the region growing operation provides a binary 3D data field.

The step of applying a filter to the three-dimensional in vivo image includes applying a shape filter preferably, the shape used in the shape filter is a tube. The shape filter may be a multi-scale shape filter. The shape filter may be a Hessian-based filter, preferably applied as per Frangi 1998.

The step of performing the automated geometric analysis may include comparing the scale at a first position in the vasculature tree to the scale at a second position in the vasculature tree preferably, the first position and the second position are located in the same vessel branch of the vasculature tree.

The step of performing the automated geometric analysis may include calculating the change in scale along a length of a branch in the vasculature tree, preferably calculating the change in diameter along the entire length of an entire generation of the branch, or calculating the change in diameter along the entire length of the branch of the vasculature tree. The method may include performing automated geometric analysis throughout the entire segmented vasculature tree (i.e. in each branch of the segmented vasculature tree).

The method may include acquiring a three-dimensional in vivo image in the absence of contrast agent. The step of acquiring a three-dimensional image may include acquiring a series of two-dimensional in vivo images and reconstructing a three-dimensional image from the two-dimensional images, preferably acquiring the two-dimensional images using X-ray radiation, preferably reconstructing the three-dimensional image using computed tomography.

The method may include scanning for an embolism, such as a pulmonary embolism. The method may include scanning for a vascular irregularity in the lung vasculature. The method may include acquiring a three-dimensional in vivo image of the lungs. The detected irregularity may be indicative of pulmonary embolism. The method may include analysing the geometry to classify segments of the vasculature as normal or irregular. The method may include analysing the geometry to detect an occlusion or partial occlusion. The method may include providing a visualisation of the vasculature indicating areas of vessel irregularity, for example pulmonary embolism. The method may include inverting the three-dimensional image before the filtering step.

In yet a further aspect of embodiments described herein there is provided a method of scanning for vascular irregularities, the method including: acquiring a three-dimensional in vivo image in the absence of contrast agent; applying a multi-scale shape filter to the three-dimensional in vivo image to provide a probability field and a scale field, the probability field representing the probability that a voxel in the three-dimensional in vivo image is a part of a tubular structure and the scale field representing the filter size that yields the greatest probability that the voxel belongs to a tubular structure; and performing an automated analysis on the probability field and the scale field to detect irregularities in the vasculature.

The method may include performing vessel segmentation on the probably field to extract a vasculature tree from the three-dimensional in vivo image, mapping the scale field to the segmented vasculature tree to quantify the geometry of the vasculature tree; and performing an automated geometric analysis on the calculated geometry to detect irregularities in the vasculature.

In yet a further aspect of embodiments described herein there is provided a method of scanning for a pulmonary embolism, the method including: acquiring a three-dimensional in vivo image in the absence of contrast agent; applying a multi-scale shape filter to the three-dimensional in vivo image to provide a probability field and a scale field; performing vessel segmentation on the probably field to extract a vasculature tree; mapping the scale field to the segmented vasculature tree to quantify the geometry of the vasculature; and calculating the change in scale along a length of a branch in the vasculature tree to detect irregularities in the vasculature.

In yet a further aspect of embodiments described herein there is provided a method of scanning for a pulmonary embolism in the lung vasculature, the method including: acquiring a series of two-dimensional in vivo chest X-ray images in the absence of contrast agent; reconstructing a three-dimensional image from the two-dimensional chest X-ray images; applying a Hessian-based multi-scale shape filter as per Frangi 1998 to provide a probability field and a scale field; segmenting a vascular tree from the probability field by performing a region growing operation on the probability field; skeletonising the vasculature tree by extracting the centreline of each branch in the vasculature tree; mapping the scale field to the skeletonised vasculature tree to provide the scale of the vessel at each point in the skeletonised vasculature tree; and calculating the change in scale along the centreline in a length of a branch in the vasculature tree to detect a pulmonary embolism.

In yet a further aspect of embodiments described herein there is provided a system for detect irregularities in the vasculature, the system comprising: an energy source to pass energy through a sample comprising vasculature; an imaging system to record two-dimensional in vivo images of the energy that passes through the sample in the absence of contrast agent, the imaging system recording images at multiple projection angles; a computed tomography system to reconstruct the two-dimensional images into a three-dimensional image; an analysing system to filter the three-dimensional in vivo image to provide a probability field and a scale field, the analysing system performing an automated analysis on the probability field and the scale field to detect irregularities in the vasculature.

The analysing system may perform vessel segmentation on the probably field to extract a vasculature tree from the probability field, maps the scale field to the segmented vasculature tree to quantify the geometry of the vasculature tree, and performs an automated geometric analysis on the calculated geometry to detect irregularities in the vasculature. The analysing system may apply a Hessian based multi-scale shape filter to provide the probability field and the scale field. The analysing system may be located off site from the imaging system.

In yet a further aspect of embodiments described herein there is provided a method of calculating a ventilation/perfusion measure from a three-dimensional in vivo lung image in the absence of contrast agent and a time series of lung images, the method including: applying a filter to the three-dimensional in vivo lung image to provide a probability field and a scale field; performing vessel segmentation on the probably field to extract a vasculature tree from the probability field; mapping the scale field to the segmented vasculature tree to quantify the geometry of the vasculature tree; measuring the motion of a portion of the lung from the time series of lung images; comparing the motion of the portion of the lung to the scale of the vasculature in the region of the portion of the lung to obtain a ventilation/perfusion measure.

The method may include measuring the displacement of the portion of the lung. The method may include measuring the expansion of the portion of the lung. The motion may be measured at multiple points in the portion of the lung, and the multiple measurements can be averaged. The scale for the comparison may be measured at the boundary of the portion of the lung. Alternatively, the scale for the comparison may be measured at the centre of the portion of the lung.

The method may include measuring the motion of multiple portions of the lung, and performing the comparison at each of the multiple portions. The ventilation/perfusion measure of a first portion can be compared to the ventilation/perfusion of a second portion.

The method may include locating the portion of the lung at an endpoint of the segmented vasculature. The method may include locating the portions of the lung at equal scales in multiple branches.

Other aspects and preferred forms are disclosed in the specification and/or defined in the appended claims, forming a part of the description of the invention.

In essence, embodiments of the present invention stem from the realization that improved image processing techniques have the capability to extract and use image data to overcome the need for contrast agents to distinguish between different types of tissue. Furthermore, it has also been realised that the image data accessed by the improved image processing can be used to identify irregularities in vessels. While specific methods of processing data from images are disclosed in the prior art, the specific combination of methods and method steps have not hitherto been used.

Advantages that may be provided by some embodiments the present invention comprise the following:

the method does not require the use of contrast agents, and thus avoids issues related to contrast agents such as inducement of nephropathy, the method can be applied to existing (or historical) contrast-free imaging data, existing contrast-free patient images can be used in the method, thus avoiding the need to subject the patient to further collection of images, avoiding further patient radiation exposure, and avoiding the financial cost of additional image collection, new options for rapid clinical diagnosis, significant advancement in imaging technology, improved detection of changes or irregularities in patients, improved method for imaging and quantifying vasculature, such as pulmonary vasculature.

Further scope of applicability of embodiments of the present invention will become apparent from the detailed description given hereinafter. However, it should be understood that the detailed description and specific examples, while indicating preferred embodiments of the invention, are given by way of illustration only, since various changes and modifications within the spirit and scope of the disclosure herein will become apparent to those skilled in the art from this detailed description.

BRIEF DESCRIPTION OF THE DRAWINGS

Further disclosure, objects, advantages and aspects of preferred and other embodiments of the present application may be better understood by those skilled in the relevant art by reference to the following description of embodiments taken in conjunction with the accompanying drawings, which are given by way of illustration only, and thus are not limitative of the disclosure herein. The patent or application file contains at least one drawing executed in color. Copies of this patent or patent application publication with color drawing(s) will be provided by the Office upon request and payment of the necessary fee.

DETAILED DESCRIPTION

The method of the present invention provides a means for obtaining vessel calibre measures from contrast free computed tomography (CT) images. The laboratory based imaging system discussed herein yielded images with sufficient resolution to resolve smaller blood vessels in vivo. The imaging system and method of the present invention presents an alternative angiography technique for small animal studies, and human scanning, without the need for contrast agents, and theoretically could allow repeat imaging in the same animals over time as disease processes progress or in response to treatments.

Figure 1:
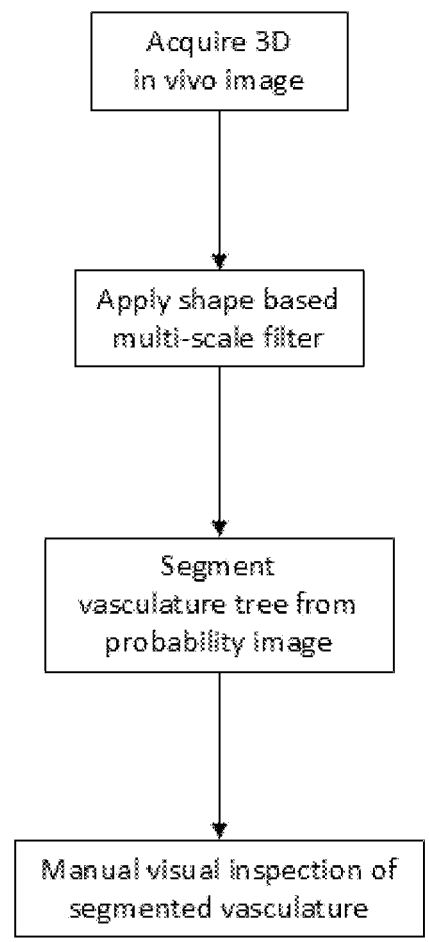
FIG. 1 is a flow chart illustrating typical method steps of the prior art in which a multi-scale filter is used on images without contrast, with the output being manually inspected
Figure 2:
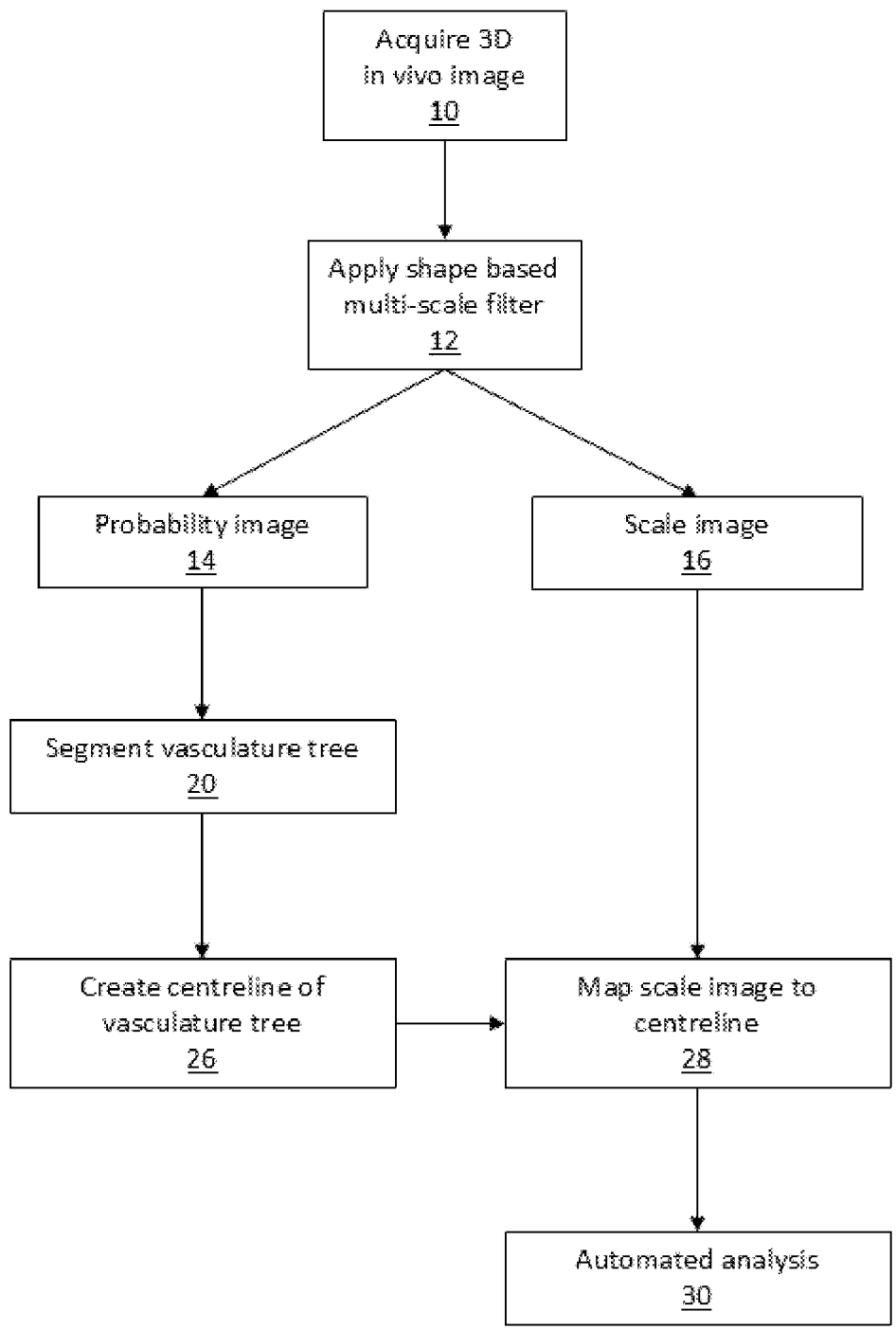
FIG. 2 depicts an embodiment of the invention that uses a multi-scale filter and vascular segmentation on images without added contrast, as described herein.
Figure 3:
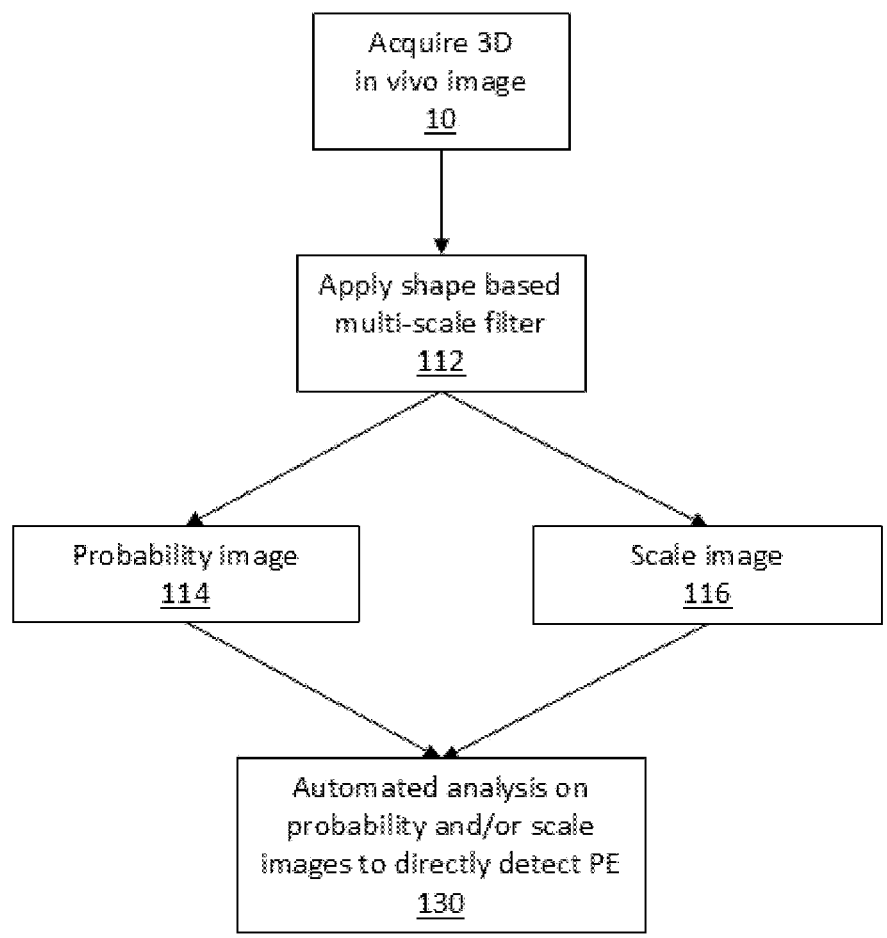
FIG. 3 depicts another embodiment of the invention wherein a multi-scale filter is used on images without added contrast, with both the probability filed and the scale field of data output from the filter being used to directly detect possible locations of PEs.

FIGS. 1 to 3 are flow charts illustrating method steps for prior art (FIG. 1), and method steps for embodiments of the invention (FIG. 2 and FIG. 3). FIG. 1 illustrates typical method steps of the prior art in which a multi-scale filter is applied to images without contrast agent in order to segment the vasculature for manual visual inspection by a user. By contrast, FIG. 2 depicts an embodiment of the present invention, as described herein, which uses a multi-scale shape filter on images without contrast agent, and performing an automated analysis on the probability data (such as a probability field), and scale data (such as a scale field) extracted from the multi-scale filter data, to detect irregularities in the vasculature, such as pulmonary embolisms. As shown in FIG. 2, this is achieved by determining the scale value at the centerline of the vasculature. FIG. 3 depicts a preferred embodiment of the method of the present invention wherein a multi-scale shape filter is used on images without contrast agent, with the probability data, shown as a probability field, and scale data, shown as a scale field, output from the filter being used to directly detect possible locations of irregularities in the vasculature, such as pulmonary embolisms.

The embodiments depicted may include, for example, the following steps:

providing one or more images of lung vasculature comprising one or more vessels, the image(s) having been captured in vivo in the absence of contrast agent. The image(s) are typically 3D and may be derived directly from a patient scan for the purpose of rapid PE diagnosis, or could for example, use historical or archived images as in the case of investigative research.

applying a filter to said images to create a probability field for the lung vasculature. Typically the filter is a shape-based multi-scale filter such as a Hessian-based multi-scale shape filter. This step may optionally be followed by carrying out flood-fill selection of the probability field for the lung vasculature to yield a binary image. This image may optionally be subjected to carrying out binary segmentations of the binary image. Vessel centrelines can then be extracted from the binary segmentation. At the centre of a vessel, the scale that gives the maximum probability of a vessel is extracted. This scale corresponds to the size of the vessel. The filter, such as a Hessian-based multiscale shape filter, provides a measure of the probability that a vessel of a given size exists at each image voxel. Accordingly, the method of the present invention may include utilising the vessel centrelines and extracting the size at which the greatest vesselness probability value exists at each centreline point.

analysing the probability field to detect irregularities in the one or more vessels. In the case of the present invention, the vessel irregularity is detected based on the changes in vessel diameter of one or more vessels in the pulmonary vasculature.

Figure 4:
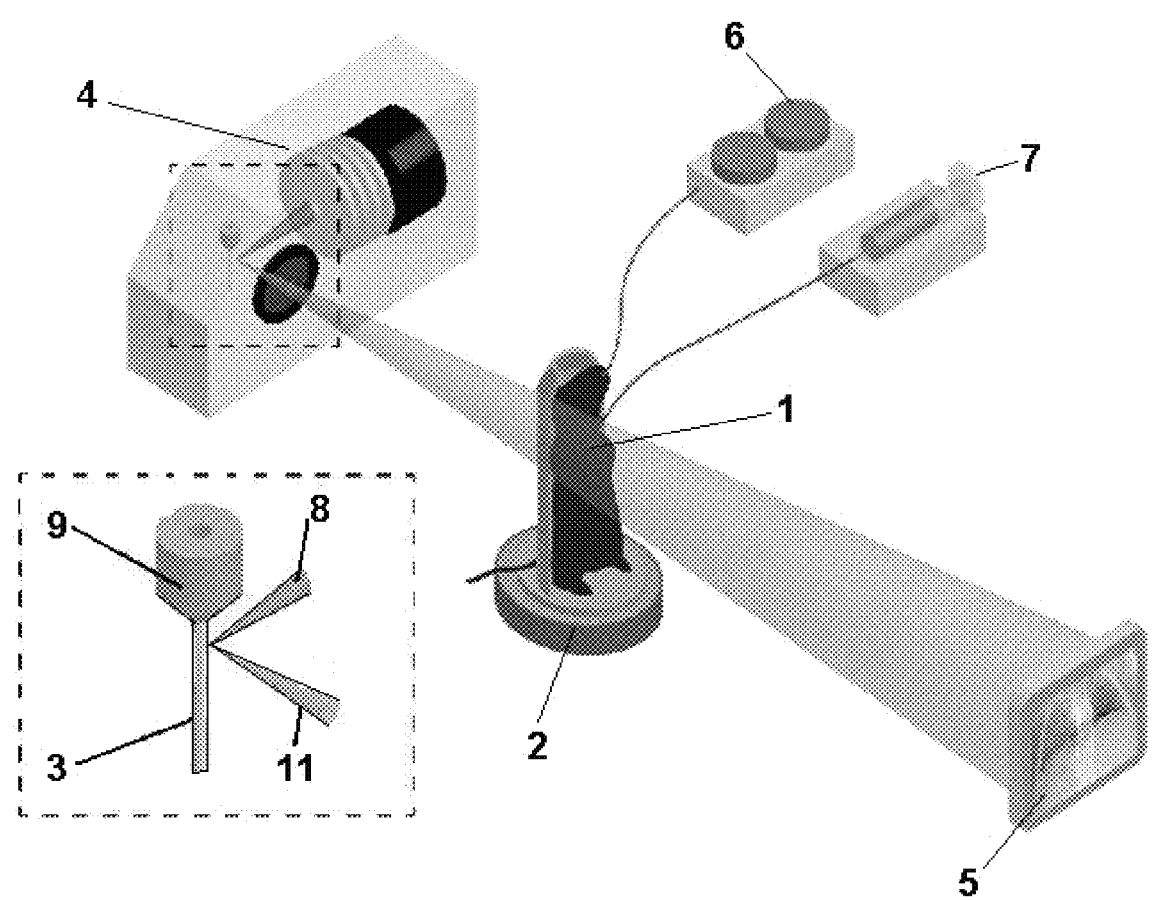
FIG. 4 illustrates an X-ray imaging setup used for small animal scanning in association with the method of the present invention. In this schematic there is depicted a BALB/c mouse (1) intubated and mechanically ventilated by a ventilator (6) and placed in a custom sample mount (2) on a rotating stage in between the liquid metal jet X-ray source (4) and structured CSi flat panel detector (5). An expanded view of the X-ray source shows the jet nozzle (9) of a liquid metal jet anode (3) relative to the incoming electron beam (8) and X-ray beam (11). The measurements calculated using the method of the present invention may be validated by 2D angiography measurements, which requires iodinated contrast agent to be injected using a micro-syringe pump (7) during a breath-hold at peak inspiration (the iodine pump is included in this figure for this reason).
Figure 5:
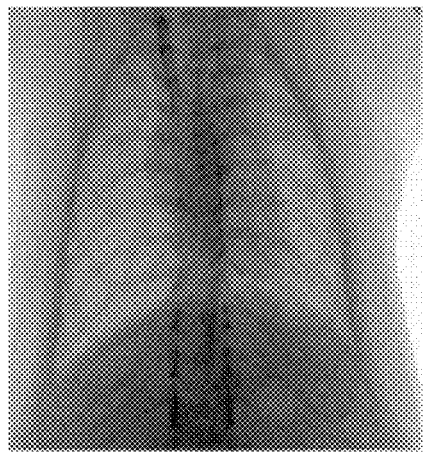
FIG. 5 illustrates a typical 2D projection image generated using laboratory X-ray source
Figure 6:
FIG. 6 illustrates a typical single slice from 3D volume reconstructed from 2D images such as the one shown in FIG. 5 (using a cone-beam reconstruction technique).

The method of the present invention has been applied to images obtained by micro-computed tomography (μCT) in live mice (n=5) under mechanical ventilation. FIG. 4 depicts an appropriate set up for imaging of this type. The method was used to quantify pulmonary vasculature calibre without the need for external contrast agents. To validate this approach the measurements were compared to contrast microangiography in the same mice.

The experimental data illustrates a benefit of the method of the present invention. Specifically, with reference to mice, the method has enabled volumetric measurements of the entire pulmonary vasculature in mice in 3-dimensions, and without the use of contrast agents or euthanasia. As such, due to the removal of contrast agent, this technique could be used for repeated imaging of animals to study changes to vasculature without the risk of premature death, which is a known problem in sensitive mouse models of disease. Furthermore, it illustrates that the method can be of value in the clinical setting for both animals and humans.

The following paragraphs describe experimental procedures and tools using a Hessian-based enhancement filter to obtain quantitative vessel calibre measures from μCT images without contrast agent.

(i) Experimental Procedure

Eight-week old BALB/c female mice (n=5) were anesthetized with intraperitoneal injections of a mix of ketamine and xylazine (150 mg/kg and 10 mg/kg respectively). Mice were orotracheally intubated and allowed to continue breathing spontaneously while a customized 24-gauge BD Angiocath catheter was inserted into the jugular vein and advanced into the superior vena cava for administering contrast agent (Isovue 370, Bracco Diagnostics) during validation (as discussed below). The mouse was securely restrained in a custom-built acrylic chassis in a supine position during the surgical procedure. Mice were then ventilated using pressure control ventilation on a custom small animal ventilator (shown in FIG. 4) with an inspiratory pressure of 20 cm.$H_2O$, zero positive end-expiratory pressure, and inspiratory and expiratory times of 300 ms each (a respiratory rate of 100 breaths/min). Tidal volumes with these settings were approximately 400 μl for a 20 g mouse, or 20 μl/g (20 ml/kg). Mice were given a subcutaneous bolus of 100 μl saline twice and ventilated for 10 minutes prior to imaging to allow equilibration and lung recruitment. Mice were kept warm using pocket warmers wrapped around the lower abdomen and legs.

(ii) Imaging Protocol

Imaging was conducted in the Laboratory for Dynamic Imaging at Monash University (Melbourne, Australia). The X-ray imaging setup consists of a high brightness X-ray source (Excillum AB) that uses an X-ray beam generated from liquid metal jet X-ray technology (70 kV, 265 W) with a 15 μm spot size. A high speed CMOS flat-panel detector was used to capture images at a frame rate of 30 Hz (exposure of 15 ms). The mouse was positioned in the acrylic chassis in front of the X-ray beam in the upright position. A high precision rotary stage (Zaber Technologies) was used to rotate the mice 400 degrees under mechanical ventilation for the CT scan. The imaging was synchronised with the mechanical ventilation trace, and μCT of breathing mice was performed to obtain 4D data of the lungs at 15 different time points in the respiratory cycle. Each timepoint in the 4DCT scan consists of 800 2D projection images. A calibration scan of an acrylic cylinder with fiducials was performed before and after mouse scans. This process captures the tilt angle and centre of rotation of the scan necessary for accurate CT reconstruction results. The source-to-isocentre of the rotation stage and source-to-detector distances were 325 mm and 3325 mm respectively. The effective isotropic voxel size of the imaging system was 19.4 μm.

(iii) 3-Dimensional CT Image Reconstruction and Analysis

As the image acquisition was synchronized with mechanical ventilation, the point in the respiratory cycle for each image was known and the data was binned against the mechanical ventilation trace. In other words, images that were acquired at the same point in the breathing cycle, over multiple breaths, were placed into a bin of similar images. The 2D projection images in each bin for a given phase in the respiratory cycle were reconstructed using a cone-beam reconstruction technique to obtain 3D volumes, or images, at different points in the respiratory cycle.

A vesselness image filter based on Frangi et al. (Frangi et al, Medical Image Computing and Computer-Assisted Interventation—MICCAI'98 (eds. Wells, W. M., Colchester, A. & Delp, S.) 130-137 (Springer, 1998) accessible at http://link.springer.com/chapter/10.1007/BFb0056195) was applied to the CT volume at peak inspiration (when the contrast ratio between the lung vasculature and the lungs themselves is the greatest). Using a Gaussian kernel over multiple scales (discrete cosine transform, also referred to as the DCT), the Hessian image (local image gradients) was calculated. The local image gradients were matched to an ellipsoid to discriminate between plane-like structures and tubular structures. This filter produced a volume for the vesselness parameter (the probability field), a measure relating to the likelihood that any given pixel belongs to a tubular structure. The measures for vesselness were computed for each kernel scale (ranging between 4 and 20 voxels, which correspond to a range of 77.6-582 μm). By taking the scale that results in the highest value for vesselness, for each voxel, a scale field (or image) is created.

Figure 11:
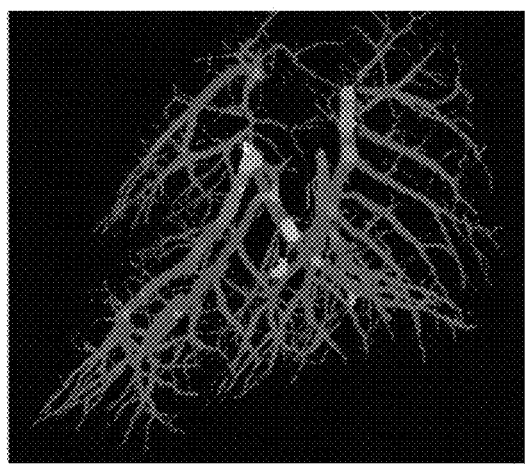
FIG. 11 illustrates the vesselness coloured by the scale value at the centreline of each point in each branch.

A flood-fill segmentation using Avizo (FEI VSG, France) was used to segment the pulmonary vasculature from the computed vesselness image at multiple scales. Up to 16 generations of branches within the vasculature tree were visible in the segmented vasculature. A skeletonization procedure (Sato, M. et al, TEASAR: tree-structure extraction algorithm for accurate and robust skeletons, 8th Pacific Conference on Computer Graphics and Applications, 2000. Proceedings 281-449 (2000). doi:10.1109/PCCGA.2000.883951) was used to compute the centerline in each branch of the segmented pulmonary vasculature. Values from the scale field are then mapped to the centreline of the pulmonary vasculature. In other words, the position of each voxel in the centreline data is noted, and the corresponding scale value at that voxel is extracted from the scale image and associated with the point in the centreline. FIG. 11 shows a composite image after incorporating the Gaussian scale and the segmented pulmonary vasculature by colouring each vessel with the centreline scale value.

(v) Validation of the Embodiment of the Invention

Figure 7:
FIG. 7 is an unprocessed X-ray projection image of iodinated contrast agent in the lung vasculature (angiography trace with an iodine bolus administration), which has been used to validate the contrast-free vessel quantification method according to the present invention.
Figure 8:
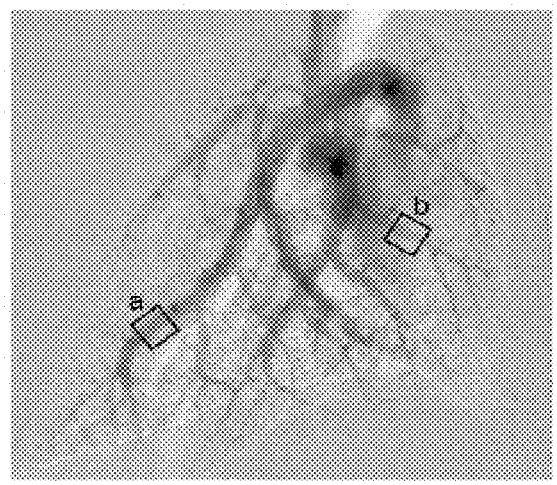
FIG. 8 is a filtered version of FIG. 7. Background correction and a moving average is used to enhance the contrast intensity in the image.

To validate the proposed method, 2D microangiography using contrast agent was performed (FIGS. 7 to 9) on the same mice from three different views. The images are pre-processed using a digital subtraction and averaging scheme to enhance the intensity of the pulmonary arteries. FIGS. 7 and 8 show images obtained from microangiography before and after processing, respectively.

FIG. 7 is an image taken ~0.6 s after contrast administration. Both CT (the method of the invention) and 2D angiography (the validation method) were conducted in seven BALB/c mice, but the angiography procedure failed in two of the mice, and therefore only five mice had both procedures. Failure to correctly place the catheter tip at the superior vena cava is one disadvantage of the microangiography approach, which is eliminated with the new method according to the present invention.

For 2D angiography imaging, iodinated contrast agent was injected via the jugular vein cannula with a microinjection pump that was programmed to deliver a bolus administration of 0.12 ml of iodine contrast agent at a speed of 10 ml/min. Image acquisition was initiated 1 s before iodine injection, and 200 frames were recorded for each scan. The lung vessels were imaged when ventilation was interrupted for a 5 s breath hold at peak inspiration to eliminate any blurring from lung movement. Mice were given at least 5 min to recover from each injection of contrast agent. Angiography was performed three times for each mouse: right anterior oblique, left anterior oblique, and frontal views (without rotation during imaging), in increments of 45 degrees.

The sequence of angiography images was analysed using both custom in-house software and tools from FIJI (Schindelin, J. et al. Fiji: an open-source platform for biological-image analysis. Nat. Methods 9, 676-682 (2012)). A background correction using the averaged image of the entire sequence was performed to enhance the intensity of the iodinated vessels within the image. To stabilize the changes to pixel intensities from changes in relative iodine levels within the vessels, a temporal moving average filter (five images either side) was applied to the background corrected image sequence.

With angiography, contrast medium was only highly visible in the arteries following a bolus injection. As a result, only pulmonary artery calibre measures are validated in this study. A total of 490 pulmonary arterial diameter measurements were obtained for five mice.

With 2D angiography images, electronic calipers were used to obtain 10 line profiles (FIGS. 7 & 8) around the vessel of interest. A frame from the processed image sequence (FIG. 8) in which the vessels were most intensely filled with contrast agent was chosen for 2D angiography measurements. The edge of the vessel was determined to have the steepest change in pixel intensity. Table 1 shows results from a linear regression on individual mouse data sets. Mouse 2 in the study had irregular contrast distribution resulting in only 15 measures for arterial diameter using microangiography.

For comparative purposes, the kernel scale (DCT) which resulted in the maximum value for vesselness was mapped in to the 3D volume using the points on the skeleton. This 3D volume was forward projected to create a composite image (FIG. 11) of the segmented vasculature tree coloured by DCT. For clarity, the diameter of the vessel shown in the figure was the centreline tree thickness from the skeletonisation algorithm. The volume was projected in increments of 45 degrees to match the right anterior oblique, left anterior oblique and frontal views obtained with 2D angiography. A probing tool is used to measure values for DCT from the composite image at regions of interest that correspond to line measures from 2D angiography.

Figure 9:
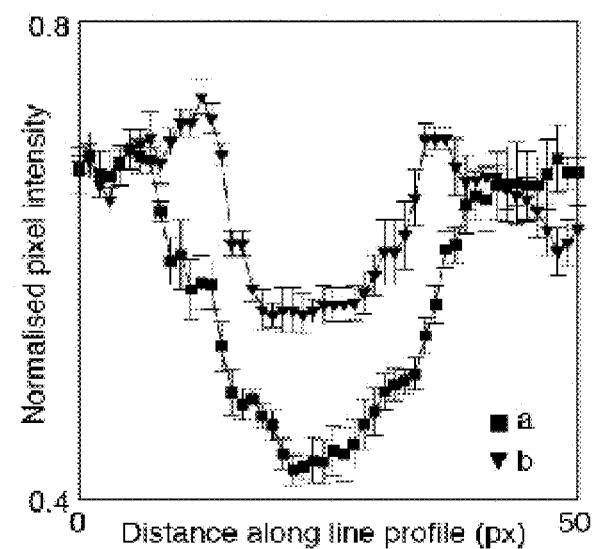
FIG. 9 is a plot of line profiles of two vessels shown in FIG. 8 (indicated as 'a' and 'b' in FIG. 8). The plot shows the change in pixel intensity across the line profile. Symbols represent mean intensity and error bars represent s.e.m. of 10 line profiles obtained along the vessel within the limits of the black boxes ('a' and 'b').
Figure 10:
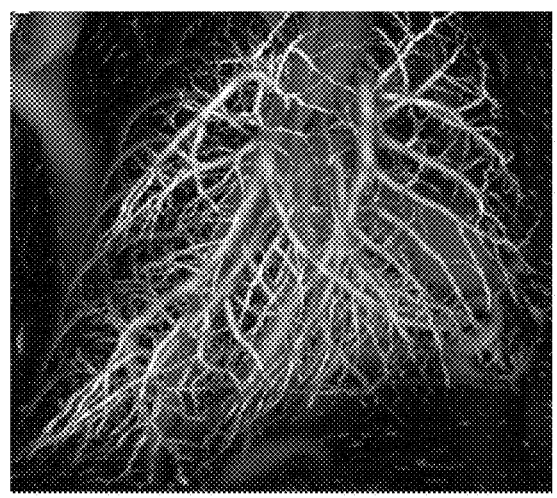
FIG. 10 illustrates the 'vesselness' (or probability field), as calculated from the multi-scale shape filter according to the method of the invention.
Figure 12:
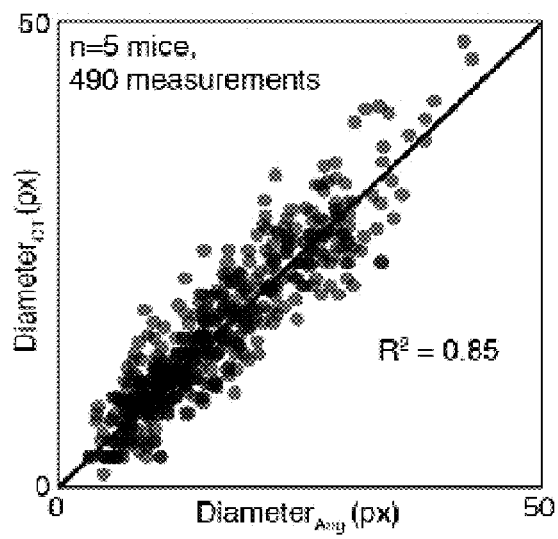
FIG. 12 is a plot, for validation, of vessel calibre measurements of the present invention from a contrast-free CT volume (vertical axis) against vessel calibre measurements using electronic calipers (i.e. software to measure the size of a feature in an image) from 2D angiography images (horizontal axis). The straight line represents the position in the plot where the measurements of the present invention equal the angiography measurements.

The points and error bars on the line plots in FIG. 9 represent mean±SEM. Linear regression was used to determine the relationship between DCT and DAng for individual mice. Table 1 summarizes the regression data for the mice imaged in this study. FIG. 12 shows measurements obtained for all mice in the study after correction using linear regression.

The proposed method yielded a satisfactory vasculature tree highlighting its benefit over measures using contrast agents. Validations show that there is a good correlation between the vessel calibre measurements from 2D angiography and the contrast-free CT method ($R^2$=0.85) of the present invention.

TABLE 1

| Mouse # | DCT (px) | $R^2$ | n |
|---|---|---|---|
| 1 (22) | 0.41DAng + 4.51 | 0.87 | 65 |
| 2 (23) | 0.49DAng + 3.51 | 0.81 | 15 |
| 3 (24) | 0.47DAng + 3.63 | 0.75 | 60 |
| 4 (34) | 0.31DAng + 2.90 | 0.77 | 206 |
| 5 (37) | 0.42DAng + 2.32 | 0.83 | 48 |

Figure 13:
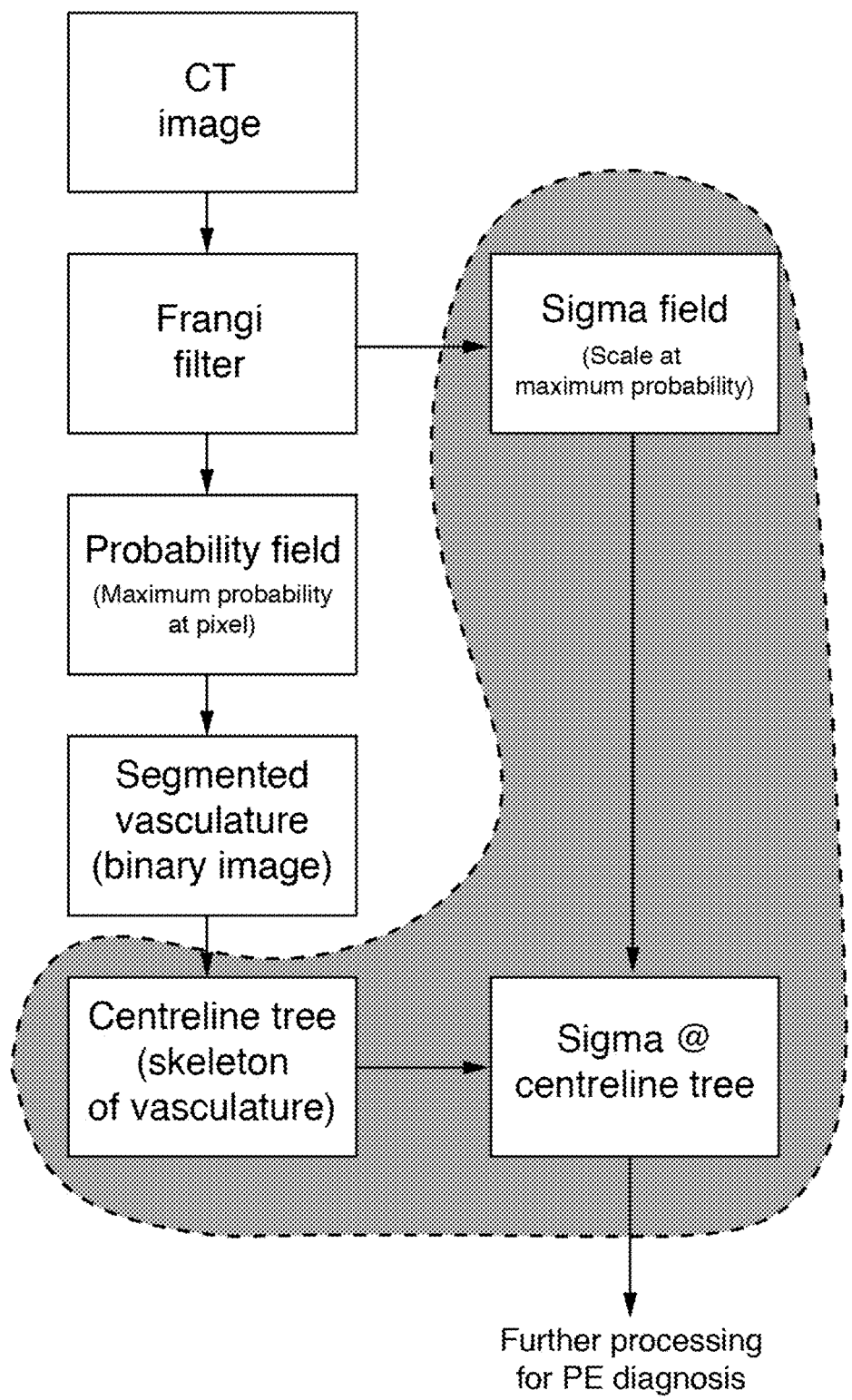
FIG. 13 is a flow chart illustrating the method steps used in the embodiment of the invention as described in the experiment described in the following paragraphs.

FIG. 13 is a flow chart illustrating the method steps used in the embodiment of the invention as described above.

Although the present invention has been demonstrated with reference to improved analysis of pulmonary perfusion patterns in murine models of lung disease, it is readily apparent that the method of the present invention has clinical applications for both human and animal patients. Specifically, the method provides a non-contrast approach to generate high fidelity, 3D quantification of the pulmonary vasculature that enables the detection of abnormalities in pulmonary vasculature, such as the abnormalities that correlate with PE.

For example, a human scanner, such as a Cone Beam CT (CBCT) scanner, could be used to acquire a series of 2D chest X-ray images, at multiple viewing angles, as a patient freely breathes. The images are acquired without the addition of contrast agent to the patient's blood stream, thereby avoiding known adverse side effects from the administration of contrast agent, such as contrast medium induced nephropathy (CIN). From the time series of X-ray images a CT reconstruction is performed on only the 2D images that were acquired at peak inspiration (when the signal to noise ratio between the lung vasculature and the lungs themselves is the greatest), thereby forming a single CT of the lungs at peak inspiration (when the lungs are stationary or nearly stationary). Alternatively, the CT may be performed as a "breath hold", in which the patient holds their breath during the scan, preferably at peak inspiration, so that the images don't need to be selected from the CT scan. Furthermore, in order to provide greater CT resolution, the breath hold CT scan may be "gated" to the cardiac cycle, in order to remove the movement of the heart, which has a physical impact on the lungs, from the images, and therefore from the CT scan on which the filtering is performed.

The CT reconstruction technique that is used can be any known standard CT reconstruction, such as cone beam computed tomography (CBCT). The reconstruction creates a series of 2D planar slices, which can be combined to form a 3D image 10 of the lungs and lung vasculature. Alternatively, modern CT scanners, such as helical or spiral CT scanners, may directly output a 3D image 10, which can also be used for analysis.

Once the 3D image 10 has been reconstructed (or directly provided from a CT machine) image filtering can be performed to extract the data of interest from the images. In particular, a shape-based filter is performed on the 3D image. The shape based filter is applied to every voxel in the 3D image in order to determine the probability that the voxel in the image, at a given scale, is part of the specified shape. This produces a probability field (also known as a probability image) of the scale. The shape based filter can be applied at multiple scales (i.e. a multi-scale shape filter 12), thereby creating multiple probability fields, one for each scale. This creates probability data and scale data that can be interrogated to scan for vasculature irregularities. An overall probability field (or image) 14 can be formed by combining the multiple single scale probability fields. This is conducted by comparing the probability of the first voxel in each of the probability fields and selecting the highest probability, comparing the probability of the second voxel in each of the probability fields and selecting the highest probability, and so on for all voxels.

The scale at which the highest probability occurs is also recorded for each voxel, thereby creating a corresponding overall scale field 16 (or image). The terms field and image are used here somewhat interchangeably when referring to the probability and scale fields, as the data in the probability and scale fields can be displayed visually, as an image. Essentially the probability field represents the probability that a voxel in the three-dimensional in vivo image is a part of the shape of interest, and the scale field represents the filter size that yields the greatest probability that the voxel belongs to the shape of interest.

The multi-scale shape filter 12, preferably based on Frangi et al. (as specified above), can be used to detect shapes such as plate-like structures, tubular structures, blob structures, etc. For example, when investigating the vasculature of the lungs the shape based filter will interrogate the 3D image 10 for tubular shapes or structures. In addition, because the vessels in the lung are not of a single diameter, the shape-based filter is run at multiple scales, in order to capture tubular structures at multiple diameters.

The overall probability field 14 and scale field 16 are then created as described in the previous paragraph. In other words, the probability field 14 will represent the probability that a voxel in the three-dimensional in vivo image is a part of a tubular structure (also known as vesselness), and the scale field 16 will represent the most likely diameter tube that each voxel is part of. In order to simplify implementation of the multi-scale shape filter 12 the image may be inverted before the filter is applied to the 3D image (as shown in FIG. 2). Alternatively, the filter may be designed to effectively invert the image in the application of the filter (i.e. the inversion may be carried out as part of the filtering process).

Regarding performing the filter at multiple scales, the shape-based filter can be performed using 2 to 100 scales, 5 to 50 scales, 10 to 40 scales, 10 to 20 scales, 15 to 20 scales, or preferably 18 scales, in order to adequately define the vasculature of the lung. The scales may correspond to vessel sizes of 0.2 mm to 30 mm, 0.2 mm to 10 mm, 0.5 mm to 30 mm, 0.5 mm to 20 mm, 0.5 mm to 5 mm, 1 mm to 20 mm, 1 mm to 10 mm, or 1 mm to 2 mm. The scales may be equally divided in the vessel size range, or they may be distributed to capture known common diameters of blood vessels. In addition, the number of scales used to calculate the probability field may be different from the number of scales used to calculate the scale field. For example, 30 scales may be used to calculate the probability field and then 3000 scales may be used to calculate the scale field. In other words, the scale field may be calculated using a higher number of scales to produce a higher resolution scale field. In other words, the multi-scale shape filter may be applied in two stages, a first coarse scale (e.g. 18 scales) to produce the probability field, and a second fine scale (e.g. 180 scales) to produce the scale field.

Referring to the method shown in FIG. 2, once the overall probability image 14 has been constructed the vasculature tree can be segmented 20 from the 3D image 10. This is achieved by performing a region growing operation on the probability field to provide a binary image (or data field) of the lung vasculature. Both the arteries and the veins can be extracted by using this technique, and depending on the vascular irregularities of interest a user may choose to only extract either the arteries or the veins. For example, emboli generally become stuck in veins, except for in the lungs, where they only become stuck in the arteries.

The region growing operation is a flood fill or form filling operation. This step is performed by choosing a recognisable portion of the lung vasculature in the probability image 14, with the form filling operation connecting the branches in the vasculature tree. As an example, the region growing operation can be a flood-fill segmentation using Avizo (FEI VSG, France). This process results in a binary image that has a single flood-filled section, thereby segmenting the vasculature from the original 3D CT reconstruction. In this way the probability field is both binarised and segmented in a single step. It will be understood that this could be carried out in two separate steps, if desired.

Once the vasculature has been segmented a skeletonisation procedure 26 is used to determine the centreline in each branch of the segmented vasculature. For example, the skeletonisation procedure may be the same technique used in Sato, M. et al, TEASAR: tree-structure extraction algorithm for accurate and robust skeletons, 8th Pacific Conference on Computer Graphics and Applications, 2000. Proceedings 281-449 (2000). doi:10.1109/PCCGA.2000.883951. This provides a skeletonised vascular tree (also referred to as a centreline tree).

Once the skeletonised vasculature tree 26 has been extracted from the probability field the scale field 16 is mapped 28 onto the skeletonised vasculature tree 26, thereby quantifying the geometry of the vascular tree. In other words, everywhere along the skeletonised vasculature tree 26 the corresponding scale value is extracted from the overall scale field 16, thereby providing a single combined 3D data set 29 (or image) with geometrical information including positional information (from the skeletonised vasculature tree 26 which was extracted from the probability field 14) and relative size information (from the scale field 16). Another way of conceptualising this step is that the skeletonised vasculature tree 26 is used as a mask on the overall scale field 16, in order to extract information on the diameter of the vessel from the scale field 16 only at the points present in the skeletonised vasculature tree 26. The scale relates to a measure of the diameter, or calibre, of the vessel, in voxels. In this way the diameter of the vessels is measured from the scale value, rather than measuring the diameter in the segmented vasculature (which is also possible). If the voxel size is known then the scale can be converted into a measurement in millimetres (or any other desired length unit). Calibration of the system can be performed by scanning tubes of known diameters in order to determine the voxel size.

Once the scale field 16 has been mapped 28 to the skeletonised vasculature tree 26 an automated analysis 30 is performed on the combined data set 29 to detect irregularities in the vasculature. This may include, for example, scanning for an embolism, such as a pulmonary embolism, or scanning for a vascular irregularity in the lung vasculature (e.g. where the detected irregularity is indicative of pulmonary embolism). This analysis is performed automatically, for example by a computer, and does not need a user to identify the location of the irregularity. In order to detect irregularities, such as PE, the automated analysis 30 includes comparing the scale at a first position in the vasculature tree to the scale at a second position in the vasculature tree. Preferably the first and second positions are located in the same vessel branch of the vasculature tree, and more preferably the first and second positions are adjacent to each other.

It will be understood that the diameter of a healthy vessel in the vasculature tree will inherently change diameter as the vasculature tree branches out. The automated analysis 30 therefore compares the change in diameter and searches for unexpected changes in the vasculature (i.e. unexpected for a healthy vasculature tree), or for known patterns of vessel ill health. The automated analysis may include comparing the scale at three (or more) consecutive points in a single branch in order to determine a trend of the change in scale (or diameter). For example, the automated analysis could include calculating the rate of change along a vessel, calculating the direction of change along a vessel, searching for a decrease followed by an increase, or searching for an increase followed by a decrease.

It is envisaged that the automated analysis can include calculating the change in scale along a length of a branch in the vasculature tree, preferably along the entire length of the branch of the vasculature tree, and more preferably throughout the entire segmented vasculature tree. The analysis may also include classifying segments of the vasculature as either normal or irregular. The analysis may also include analysing the geometry to detect an occlusion, or partial occlusion, of a vessel. One approach to conduct these classifications is through application of a fitting function or spline or similar to the diameter data, and to search for features in the data fit rather than in the raw data itself. This may be particularly useful when looking for changes in the diameter. (As per Fouras, A., & Soria, J. (1998) Accuracy of out-of-plane vorticity measurements derived from in-plane velocity field data, Experiments in Fluids, 25, 409-430.).

Once the automated analysis 30 has been completed the results may be displayed to a user (e.g. a doctor). The results can be displayed as a visualisation on a computer screen (e.g. 2D or 3D visualisation), or as a report (e.g. a hard or soft copy report). It is envisaged that the results may be displayed as an overlay on the original three-dimensional image 10 of the vasculature. For example, areas in which vessel irregularity have been identified may be highlighted to bring these areas to the attention of the doctor, thereby enhancing the doctor's ability to quickly and accurately detect vasculature problems, such as pulmonary embolism. Alternatively, the results may be displayed as a colour coded image of the segmented vasculature, with the colour coding representing the scale (or diameter) of the vasculature. It is envisaged that many other variables could also be used to display the results of the automated analysis 30, such as change in diameter, etc. In other words, the method may include providing a visualisation of the vasculature indicating areas of vessel irregularity (e.g. where the irregularity is pulmonary embolism).

Referring to the method shown in FIG. 3, FIG. 3 shows a method of scanning for vascular irregularities in a three-dimensional in vivo image 10 in the absence of contrast agent, the method including: applying a filter 112 to the three-dimensional in vivo image 10 to provide probability data (shown as a probability field 114) and scale data (shown as a scale field 116); and performing an automated analysis 130 on the probability field and/or the scale field to detect irregularities in the vasculature.

It will be understood that once the probability 114 and scale 116 fields have been created from the multi-scale shape-based filter 112 there are multiple ways for combining the data to probe for vessel anomalies, such as PE. For example, instead of segmenting and skeletonising the vasculature tree (as shown in FIG. 2), the probability filed 114 and the scale field 116 can be directly, or more directly, interrogated and combined to detect vessel irregularities or anomalies (as shown in FIG. 3). For example, it is possible to directly search for a "signature" scale pattern (e.g. that is representative of PE) in the scale field 116. The "signature" scale pattern could be determined by performing the method shown described above in relation to FIG. 2 for a number of initial patients, and identifying the pattern that is representative of PE. Once the signature has been identified it can be used to directly search the scale field 116 for that signature pattern.

Alternatively, instead of segmenting the vasculature tree, the probability field 114 could be used to mask the scale field 116. This can be achieved by applying a thresholding step to the probability field 114 (to extract the approximate position of the vasculature), and then using the thresholded probability field to mask the scale field 116. This essentially creates a scale field 116 with scale data only in locations where the thresholding step approximates the vasculature tree to be located. From such a masked scale field the vessels would appear as a "bowl-type" shape (an artefact of the filter), which can then be used to determine vessel location and size, on which the automated geometric analysis 30 can be performed.

An advantage of not including the step of segmenting the vasculature is that the computational time is decreased. It also removes the flood filling step, which may require a user to manually identify a portion of the vasculature tree. As a result, the method of detecting irregularities without segmenting the vasculature may provide a fast and user-free analysis of the three-dimensional image.

Referring now to the apparatus that would be used to acquire images of a human, it is envisaged that a similar set-up as shown in FIG. 4 could be used for a human scanner, in which the patient is rotated on a rotational stage. Alternatively, the apparatus could instead rotate the X-ray source and X-ray detector around the patient, who would remain stationary, as is done in standard CT imaging. In order to reduce the radiation dose during acquisition of the CT images a gating technique may be used so that images are only acquired, and X-ray radiation is only delivered, during peak inspiration.

It is envisaged that the three-dimensional in vivo image may be acquired by one user, such as a hospital technician, and analysed (i.e. the steps of applying the filter and performing the analysis) by another user, such as an analysis company. In other words, the method for the first user is to acquire a three-dimensional in vivo image 10 in the absence of contrast agent (which may be a simple standard CT, such as a helical or spiral CT), and the method for the second user is to apply a filter 12, 112 to the three-dimensional in vivo image 10 to provide a probability field 14, 114 and a scale field 16, 116, and to perform an automated analysis 30, 130 on data from the probability field 14, 114 and the scale field 16, 116 to detect irregularities in the vasculature. It is therefore envisaged that the analysing system (i.e. hardware, software, etc.) may be located off site from the imaging system (e.g. CT scanner), and that the method may include acquiring the three-dimensional image 10 at a first location and sending the three-dimensional image 10 to a second location (e.g. an off-site location) for analysis 12, 30, 112, 130.

Figure 14:
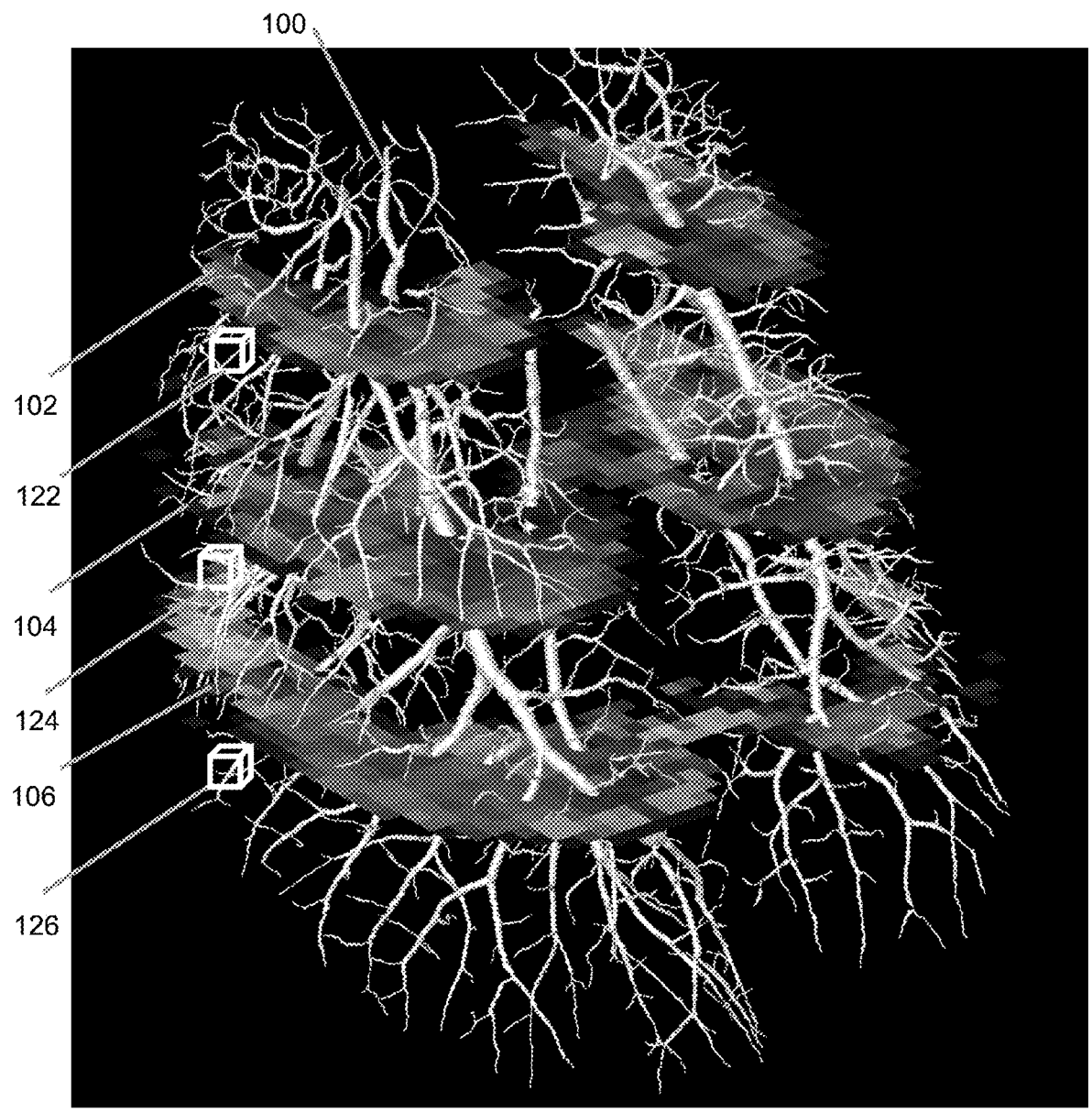
FIG. 14 is an isometric view of the segmented vasculature with regional motion information overlayed at three slice positions.

Referring now to FIG. 14, it is envisaged that the detailed geometric information from the method described herein could be combined with local (or regional) motion measurements in order to calculate a surrogate of the ventilation/perfusion (V/Q) ratio (hereafter simply referred to as V/Q or ventilation perfusion). In particular, the motion of a portion 122, 124, 126 of the lung can be compared to the scale of the vasculature in the region of the portion 122, 124, 126 of the lung to obtain a ventilation/perfusion measure.

FIG. 14 shows the segmented vasculature 100 with motion information overlayed at three slice positions 102, 104, 106 (e.g. in multiple portions of the lung). The vessel calibre information can be used as an estimate of the blood flow to a particular region (indicative of perfusion), and can be combined with local motion measurements (indicative of ventilation). Such measurements would require both a three-dimensional in vivo lung image (for vasculature tree information) and a time series of lung images (for motion measurements). The three-dimensional in vivo lung image can be acquired as described above (e.g. a CT scan). The series of lung images could be only two images (from which lung motion at that point in the respiration cycle can be determined), or the series of lung images could include a complete respiration cycle, thereby allowing the lung motion of the entire respiration cycle to be measured. Again, as previously described, the imaging for the vasculature measurements could be gated to breathing, the cardiac cycle, or both.

The motion of a portion 122, 124, 126 of the lung can be calculated by any suitable technique however, it is preferably measured using Computer Tomographic X-ray Velocimetry (CTXV), as described in U.S. Pat. No. 9,036,887 B2, titled "Particle image velocimetry suitable for X-ray projection imaging", the entirety of which is incorporated herein by reference. CTXV uses X-ray images taken from multiple projection angles in order to measure regional three-dimensional motion of the object, in this case the lungs.

The motion tracking in CTXV is based on a well-known technique called particle image velocimetry (Ply), in which the displacement of a region is calculated by selecting a region in the first image of a time series and statistically correlating the selected region to the second image in the time series. The motion measurements can therefore be 2D or 3D measurements of displacement, velocity, expansion (or ventilation), or any other suitable motion measurement. The flow in the airways can also be calculated from the motion measurements.

CTXV is generally performed for multiple regions in the image, thereby providing regional motion measurements throughout the image. Referring specifically to lung imaging, CTXV provides multiple regional motion measurements of portions of the lung, providing local lung movement and expansion measurements. CTXV can be performed at high spatial resolution, meaning that there may be multiple motion measurements in the portion of the lung selected for comparison. If this is the case the multiple motion measurements can be added (summed) or averaged. It is also envisaged that the ventilation/perfusion will be assessed at multiple portions of the lung (i.e. there will be multiple lung portions).

Before the ventilation can be compared to the perfusion the data from the two scans are associated with each other (e.g. to compensate for different resolution scans). The two data sets are also rotationally aligned.

In order to compare the motion with the scale (i.e. the "perfusion" with the "ventilation"), the scale of the segmented vasculature is measured in a region in or around the portion 122, 124, 126 of the lung. For example, the scale of the vessel can be measured at the perimeter, or boundary, of the portion 122, 124, 126, or it can be measured at the centre of the portion 122, 124, 126. Preferably each portion 122, 124, 126 will only have a single branch associated with the portion (i.e. a portion will not have two branches extending into it). This may involve locating the portions of the lung at the endpoints of branches in the segmented vasculature. Alternatively, the portions of the lung may be located at a desired scale value (i.e. vessel diameter), with all portions being positioned at the same scale value.

By comparing the motion, or a parameter derived from the motion (specifically the expansion), and the scale in multiple portions (e.g. portions 120, 122, 124 shown in FIG. 14) of the lung a ventilation/perfusion measure is obtained throughout the lung, allowing for a regional comparison of ventilation/perfusion. This method therefore allows for the detection of heterogeneous ventilation/perfusion, a well known sign of ill lung health, such as pulmonary embolism (i.e. at a PE site ventilation is normal and perfusion is reduced, and thus the ventilation/perfusion ratio is high).

One method for evaluating the V/Q is a feeder based, tree based or anatomy based method. Regions in the lung are fed air and blood by paired airway and artery (a vein is also present). As such, the entire region of lung distal to a point in an artery or airway (i.e. the portion of interest) is largely fed from that point. By selecting a measure of ventilation and perfusion associated with the airway and artery at that location an excellent measure of V/Q is obtained for the entire region distal to that location. The vessel calibre at that location is an excellent surrogate for perfusion, and the motion measurements described above allow for measurement of the flow in an airway at the same location.

Alternatively, another method for evaluating the V/Q is a region based method. For any region of the lung (even a region that is not tree based or anatomically based—e.g. a cube of tissue such as shown in FIG. 14) statistical approaches can be taken as surrogates of ventilation and perfusion. There are several ways to provide a measure of the perfusion in a selected region. For example, the modal or mean diameter in the region could be calculated, the length or volume weighted volume of modal or mean diameter in the region could be calculated, or the combined volume of the vessel(s) in the region could be calculated. There are also several ways to provide a measure of the ventilation. For example, the total expansion summed over every voxel in the region could be calculated, or modal or mean expansion in the region could be determined.

While the method of scanning for vascular irregularities in a three-dimensional in vivo image in the absence of contrast agent has been discussed largely in relation to detecting irregularities in the lungs, it is envisaged that the method could be applied to vessels in other parts of the body. For example, the method could be applied to other organs in the body, such as the brain, heart, liver and kidneys.

While the invention was described above as allowing the patient to breathe freely during imaging, it is envisaged that the patient could instead be imaged during a breath hold. The breath hold could be controlled by the patient simply holding their breath during imaging, or could be controlled by a ventilation system. In addition, while the invention was described above as acquiring images throughout the full breathing cycle, and then only using the images that were taken at peak inspiration, it is envisaged that the imaging could be gated to peak inspiration (i.e. so that images are only acquired at peak inspiration), or any other point in the breathing cycle, as desired, in order to only acquire images at a single point in the breathing cycle, thereby reducing the dose of radiation delivered to the patient.

While the invention has been described above as utilising images acquired in the absence of contrast agent (which provides health benefits to the patient), it is envisaged that the technique could also be applied to images using contrast agent.

While the invention has been described above as utilising at least one image, 2D images and/or 3D image(s), it is to be noted that the invention may be used in conjunction with any one or any combination of multiple 2D images and/or at least one 3D image.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. The described embodiments are to be considered in all respects as illustrative only and not restrictive.

Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures.

It should be noted that where the terms "server", "secure server" or similar terms are used herein, a communication device is described that may be used in a communication system, unless the context otherwise requires, and should not be construed to limit the present invention to any particular communication device type. Thus, a communication device may include, without limitation, a bridge, router, bridge-router (router), switch, node, or other communication device, which may or may not be secure.

It should also be noted that where a flowchart is used herein to demonstrate various aspects of the invention, it should not be construed to limit the present invention to any particular logic flow or logic implementation. The described logic may be partitioned into different logic blocks (e.g., programs, modules, functions, or subroutines) without changing the overall results or otherwise departing from the true scope of the invention. Often, logic elements may be added, modified, omitted, performed in a different order, or implemented using different logic constructs (e.g., logic gates, looping primitives, conditional logic, and other logic constructs) without changing the overall results or otherwise departing from the true scope of the invention.

Various embodiments of the invention may be embodied in many different forms, including computer program logic for use with a processor (e.g., a microprocessor, microcontroller, digital signal processor, or general purpose computer and for that matter, any commercial processor may be used to implement the embodiments of the invention either as a single processor, serial or parallel set of processors in the system and, as such, examples of commercial processors include, but are not limited to Merced™, Pentium™, Pentium II™ Xeon™, Celeron™, Pentium Pro™, Efficeon™, Athlon™, AMD™ and the like), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof. In an exemplary embodiment of the present invention, predominantly all of the communication between users and the server is implemented as a set of computer program instructions that is converted into a computer executable form, stored as such in a computer readable medium, and executed by a microprocessor under the control of an operating system.

Computer program logic implementing all or part of the functionality where described herein may be embodied in various forms, including a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML. Moreover, there are hundreds of available computer languages that may be used to implement embodiments of the invention, among the more common being Ada; Algol; APL; awk; Basic; C; C++; Conol; Delphi; Eiffel; Euphoria; Forth; Fortran; HTML; Icon; Java; Javascript; Lisp; Logo; Mathematica; MatLab; Miranda; Modula-2; Oberon; Pascal; Perl; PL/I; Prolog; Python; Rexx; SAS; Scheme; sed; Simula; Smalltalk; Snobol; SQL; Visual Basic; Visual C++; Linux and XML.) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g, a RAM, ROM, PROM, EEPROM, or Flash-Programmable RAM), a magnetic memory device (e.g., a diskette or fixed disk), an optical memory device (e.g., a CD-ROM or DVD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and inter-networking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality where described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL). Hardware logic may also be incorporated into display screens for implementing embodiments of the invention and which may be segmented display screens, analogue display screens, digital display screens, CRTs, LED screens, Plasma screens, liquid crystal diode screen, and the like.

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM or DVD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

"Comprises/comprising" and "includes/including" when used in this specification is taken to specify the presence of stated features, integers, steps or components but does not preclude the presence or addition of one or more other features, integers, steps, components or groups thereof. Thus, unless the context clearly requires otherwise, throughout the description and the claims, the words 'comprise', 'comprising', 'includes', 'including' and the like are to be construed in an inclusive sense as opposed to an exclusive or exhaustive sense; that is to say, in the sense of "including, but not limited to".

What is claimed is:

1. A method of calculating a ventilation/perfusion ratio from at least one in vivo lung image comprising a vasculature tree and acquired in the absence of contrast agent and a time series of lung images, the method comprising:
    applying a filter to the at least one in vivo lung image comprising the vasculature tree to provide a probability field and a scale field;
    performing vessel segmentation on the probability field to extract a segmented vasculature tree from the probability field;
    mapping the scale field to the segmented vasculature tree to quantify a geometry of the vasculature tree;
    measuring a motion of a portion of the lung from the time series of lung images; and
    comparing the motion of the portion of the lung to the geometry of the vasculature tree in the region of the portion of the lung to obtain the ventilation/perfusion ratio.

2. The method of claim 1, further comprising measuring a displacement of the portion of the lung.

3. The method of claim 1, further comprising measuring an expansion of the portion of the lung.

4. The method of claim 1, wherein measuring the motion of a portion of the lung comprises:
    measuring the motion at a plurality of points in the portion of the lung to obtain a corresponding plurality of measurements; and
    averaging the plurality of measurements.

5. The method of claim 1, further comprising repeating the measuring and the comparing for each of a plurality of portions of the lung.

6. The method of claim 1, wherein the portion of the lung is defined by a region distal to a selected point in the segmented vasculature.

7. The method of claim 1, wherein the at least one image is any one or any combination of multiple 2D images and/or at least one 3D image.

8. A system for calculating a ventilation/perfusion ratio from at least one in vivo lung image comprising a vasculature tree and acquired in the absence of contrast agent, and a time series of lung images, the system comprising a computer configured to:
    apply a filter to the at least one in vivo lung image comprising the vasculature tree to provide a probability field and a scale field;
    perform vessel segmentation on the probability field to extract a segmented vasculature tree from the probability field;
    map the scale field to the segmented vasculature tree to quantify a geometry of the vasculature tree;
    measure a motion of a portion of the lung from the time series of lung images; and
    compare the motion of the portion of the lung to the geometry of the vasculature tree in the region of the portion of the lung to obtain the ventilation/perfusion ratio.

9. The system of claim 8, wherein the computer is further configured to measure a displacement of the portion of the lung.

10. The system of claim 8, wherein the computer is further configured to measure an expansion of the portion of the lung.

11. The system of claim 8, wherein the computer measures the motion of a portion of the lung by being further configured to:
    measure the motion at a plurality of points in the portion of the lung to obtain a corresponding plurality of measurements; and
    average the plurality of measurements.

12. The system of claim 8, wherein the computer is further configured to repeat the measuring and the comparing for each of a plurality of portions of the lung.

13. The system of claim 8, wherein the portion of the lung is defined by a region distal to a selected point in the segmented vasculature.

14. The system of claim 8, wherein the at least one image is any one or any combination of multiple 2D images and/or at least one 3D image.

* * * * *